US012653398B2

(12) United States Patent
Browne et al.

(10) Patent No.: US 12,653,398 B2
(45) Date of Patent: Jun. 16, 2026

(54) UNIVERSAL ACTUATORS TO ENHANCE OPHTHALMIC IMAGING AND STRUCTURED IMAGING

(71) Applicant: THE REGENTS OF THE UNIVERSITY OF CALIFORNIA, Oakland, CA (US)

(72) Inventors: Andrew Browne, Newport Coast, CA (US); Josiah K. To, San Diego, CA (US); William C. Tang, Irvine, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 276 days.

(21) Appl. No.: 18/610,021

(22) Filed: Mar. 19, 2024

(65) Prior Publication Data

US 2024/0315556 A1 Sep. 26, 2024

Related U.S. Application Data

(60) Provisional application No. 63/491,156, filed on Mar. 20, 2023.

(51) Int. Cl.
*A61B 3/135* (2006.01)
*A61B 3/113* (2006.01)
(Continued)

(52) U.S. Cl.
CPC .............. *A61B 3/135* (2013.01); *A61B 3/113* (2013.01); *G06T 7/00* (2013.01); *G06T 17/00* (2013.01); *G06T 2207/30041* (2013.01)

(58) Field of Classification Search
CPC ....... A61B 3/135; A61B 3/113; A61B 3/0075; A61B 3/0083; A61B 3/10; G06T 7/00;
(Continued)

(56) References Cited

U.S. PATENT DOCUMENTS

| | | | | | |
|---|---|---|---|---|---|
| 6,098,490 | A | * | 8/2000 | Kowalewski | F16C 1/18 74/504 |
| 2006/0168732 | A1 | * | 8/2006 | Makino | A01N 25/34 5/622 |

(Continued)

OTHER PUBLICATIONS

Josiah K. To et al., Modular Low-Cost Automated Facial Photogrammetry, ARVO Annual Meeting presentation, May 2021.

(Continued)

*Primary Examiner* — Mohammed A Hasan
(74) *Attorney, Agent, or Firm* — VISTA IP LAW GROUP LLP

(57) ABSTRACT

Various embodiments are disclosed of universal actuators for an imaging device or probe. The universal actuator may move the imaging device or probe in one or more of a horizontal direction, vertical direction, rotational directions (e.g., axial rotation and pivoting motions). In some embodiments, the universal actuator is configured to mount to a conventional slit lamp microscope to aid in visualizing the face and or eye(s) of a subject. In other embodiments, the universal actuator is hand-held and is used to scan an imaging probe (e.g., ultrasound probe) over the surface of an eye. The universal actuator may also be removable or separable from a base that is mounted to a slit lamp microscope allowing for both instrument-based scanning and manual scanning via the hand-held device. The imaging device or imaging probe is used to obtain 2D image data. In some embodiments this 2D data is then used to generate 3D images of, for example, the face or eye(s).

20 Claims, 28 Drawing Sheets

(51) Int. Cl.
  *G06T 7/00*     (2017.01)
  *G06T 17/00*    (2006.01)
(58) Field of Classification Search
  CPC ........... G06T 17/00; G06T 2207/30041; G06T
                            2210/41; G06T 17/10
  USPC ........................................................ 351/209
  See application file for complete search history.

(56)                    References Cited

U.S. PATENT DOCUMENTS

| | | | |
|---|---|---|---|
| 2012/0069302 A1* | 3/2012 | Juhasz | A61B 3/117 |
| | | | 351/221 |
| 2015/0081110 A1* | 3/2015 | Houston | G05D 19/02 |
| | | | 700/280 |
| 2022/0260714 A1* | 8/2022 | Tan | G01S 17/93 |
| 2022/0371182 A1* | 11/2022 | Alatorre Troncoso | |
| | | | B25J 9/1075 |

OTHER PUBLICATIONS

Josiah K. To et al., Comparison of a Photogrammetry for Anatomi-
cal CarE (PHACE) system with other affordable technologies for
3D imaging of the orbit and adnexa, ARVO Annual Meeting
presentation, May 2022.

* cited by examiner

RCS     Optic
Complex  Nerve

Composite
En Face
Scanned Area

Eye

UNIVERSAL ACTUATORS TO ENHANCE OPHTHALMIC IMAGING AND STRUCTURED IMAGING

RELATED APPLICATION

This application claims priority to U.S. Provisional Patent Application No. 63/491,156 filed on Mar. 20, 2023 which is hereby incorporated by reference. Priority is claimed pursuant to 35 U.S.C. § 119 and any other applicable statute.

TECHNICAL FIELD

The technical field generally relates actuator devices used to physically move two-dimensional imaging devices to acquire multiple images of an object at multiple angles or orientations. The technical field also pertains to actuator devices that accurately register obtained images with the position and orientation of the imaging devices so that high-resolution or precise 3D images or representations may be created.

BACKGROUND

Creating three-dimensional (3D) models of objects can be achieved by using a two-dimensional (2D) imaging device to acquire multiple images of an object from multiple angles or orientations. Devices and software that enable images of an object to be acquired from multiple angles and generate 3D models of the object have been manufactured, produced and marketed. For example, there are known hand-held scanners like the EinScan 3D scanners (Dynamism, Chicago, IL), which require manual movement of the scanners. While many imaging devices can acquire 2D images, high resolution or precise 3D models cannot be created from these 2D image(s) because perfect alignment or registration of the 2D images is not possible. Improved scanning devices are needed for the creation of 3D images or representations. These devices have particular applicability to ophthalmic applications involving imaging the eyes.

SUMMARY

In one embodiment, a universal actuator for moving an imaging device is disclosed that is removably attached to an ophthalmologist's slit lamp microscope stand. The universal actuator, in one implementation, uses automatic movement of a platform or adapter on which is mounted the imaging device (e.g., camera or probe). In one embodiment, the platform is a rotatable platform. The platform rotates at a substantially uniform rotational speed in response to a rotary motor contained in the universal actuator that drives rotation of the platform. The imaging device may include a portable electronic device with camera functionality such as a mobile phone. A series of images (or a movie) of an object is obtained as the imaging device is rotated on the platform. These may be structured-light images or conventional camera images. Software in the camera or portable electronic device then assembles the acquired 2D images to generate a 3D image, representation, or model of the object. In one embodiment, the object that is scanned is a person's face or orbital area is imaged, although it should be appreciated that other objects may be imaged.

In one embodiment, the universal actuator includes a housing that contains the electronics and a motor-driven rotating platform (rotary motor). The motor drives a rotating platform. The rotating platform contains a mount on which the imaging device (e.g., camera) is mounted. The mount is located on a radially-outward portion of the platform adapter and may include an angle so that that camera of the imaging device is positioned at an angle relative to the object to be scanned. The backside of the housing includes an interface that allows the actuator to be removably mounted on the slit lamp microscope stand. The interface includes a rear extension that includes a plurality rotatable fins or tabs. The fins or tabs are securely stored in the actuator housing when not deployed. After the universal actuator is mounted to the chin rest of the slit lamp microscope stand, the fins or tabs are rotated to secure the actuator to the slit lamp microscope stand. For example, the fins or tabs may be secured to the vertical side bars that support the chin rest.

The universal actuator is powered using a power source. The power source to provide power for the device may be a stand-alone battery or a power adapter plugged into a conventional wall outlet. The rotatable platform may operate by manual actuation or it may automatically rotate for a specified period of time or rotation(s) in response to program or set of automated instructions. In one embodiment, a remote control is provided that enables a user to start and stop rotation of the platform adapter.

The universal actuator may, in some embodiments, include a moveable stage on which the imaging device is mounted. The moveable stage may move the imaging device in the vertical and/or horizontal directions. This allows imaging scans of the eye(s) in the horizontal and vertical directions. In some embodiments, the moveable stage may be integrated on the rotatable platform to further allow for rotational motion in addition to horizontal and vertical movement.

In another embodiment, a universal actuator is provided that mounts on the base or structure of a slit lamp microscope and provides for movement of a removable imaging probe in the horizontal direction, vertical direction, and/or rotational directions. The actuator device includes a mount that allows the actuator to be mounted on a standard slit lamp microscope. The slit lamp microscope is rotated out of the way 90 degrees so the actuator can be secured to the slit lamp microscope via the mount. Vertical motion is provided by a scissor platform that is driven by a stepper motor to move the platform up and down. A linear actuator is secured atop the platform to provide for linear (horizontal) motion using a stepper motor that moves an adapter back-and-forth in a horizontal direction. The moveable adapter of the linear actuator is itself secured to a platform that holds a rotational actuator. Alternatively, the vertical and horizontal motion may be imparted by a moveable stage that includes the ability to move in both the vertical and horizontal directions. In yet another alternative, the linear actuator may support the scissor platform.

In another embodiment, a universal actuator is disclosed that houses an imaging probe such as an ultrasound probe and enables pivoting of the probe about a pivot axis. The universal actuator device may be hand-held, or it may be mountable on another device such as the slit lamp microscope stand or another actuator device that imparts horizontal and/or vertical movement. The universal actuator device has a proximal probe receiver that receives the proximal (back) end of the imaging probe. The probe receiver is coupled to a curved rack that engages with pinion gear that is powered by a motor. The motor and pinion gear may be contained in a housing or frame at the proximal end of the universal actuator. Guide rails or slots may optionally be provided in the housing that interface with a pin on the probe receiver to aid in moving the proximal probe receiver along an arc. A pivot collar engages with a distal end of the imaging probe. The pivot collar includes respective pins on opposing sides that engage with an outer distal housing or frame. The pivot collar is secured to the probe receiver and/or rack via support rods. This ensures that movement of the rack translates into well-defined pivoting of the pivot collar and imaging probe contained therein (i.e., so that the ultrasound probe and rack move as one component). The pivot collar and the imaging probe contained therein can be pivoted back and forth about the pivot axis defined at the location where the respective pins engage with the distal housing. The distal end of the imaging probe or probe head includes the imaging element that is used to capture image (s) of the object such as an eye. The probe may be, for example, an ultrasound probe. A controller (e.g., microcontroller) may be used to control the motor which in turn controls the movement of the rack and proximal end of the probe. The rack moves back-and-forth along an arc while the distal end of the probe pivots about the pivot axis defined by the pivot collar. The probe receiver and the pivot collar may be designed to accommodate any number of makes and models of probes and probe types. The sweep angle may be adjustable but is typically between 10° and 40°.

The rotational actuator includes a probe adapter that receives an imaging probe inside thereof. The probe adapter may be sized and dimensioned to accommodate a wide variety of makes, models, and types of imaging probes. The probe adapter is insertable into a rotational sleeve located in the rotational actuator. Interlocking teeth on the sleeve and the probe adapter ensure that rotation of the rotational actuator transfers torque from the rotational sleeve to the probe adapter. A motor (e.g., stepper motor) is located inside a housing of the rotational actuator and rotates a gear that rotates the sleeve via the teeth located on the periphery of the sleeve.

The universal actuator device is, in some embodiments, connected to a control box that controls the movement of the imaging probe. This includes movement in the horizontal direction, vertical direction, as well as rotational movement. The movements of the scans can be controlled by adjusting the respective speeds of the stepper motors. The rotational direction and speed may also be adjusted. Pre-programmed scan paths may also be stored in the control box and used to scan along pre-defined directional profiles. This may include the order or scans, number of scans in each direction, direction(s) of scans, the speed of each scan, and the like.

In one embodiment, a universal actuator for moving an imaging probe in a controlled manner to acquire a plurality of images of an eye includes a vertical direction actuator (e.g., scissor platform), a horizontal direction actuator (e.g., linear actuator); and a rotational actuator mounted on one of the horizontal direction actuator or the vertical direction actuator, the rotational actuator comprising a motor configured to rotate a universal rotation sleeve within the rotational actuator, wherein the universal rotation sleeve is secured to a probe adapter configured to hold the imaging probe therein.

In another embodiment, a universal actuator for moving an imaging probe in a controlled manner to acquire a plurality of images of an eye includes a housing containing a motor mechanically coupled to a pinion gear and an imaging probe receiver coupled to a curved rack engaging with the pinion gear; and a pivot collar mounted at a distal end of the housing, the pivot collar pivotably secured to the housing and forming a pivot axis.

In another embodiment, a universal actuator for moving an imaging device in a controlled manner to acquire a plurality of images of an eye or face includes a housing having a first surface for holding one or more actuators and an imaging device secured to the one or more actuators and an interface extending from a second side of the housing opposite the first side and comprising a plurality of rotatable fins or tabs located at the peripheral regions thereof.

DETAILED DESCRIPTION OF ILLUSTRATED EMBODIMENTS

Universal Actuator—Face Scanning

Figure 1A:
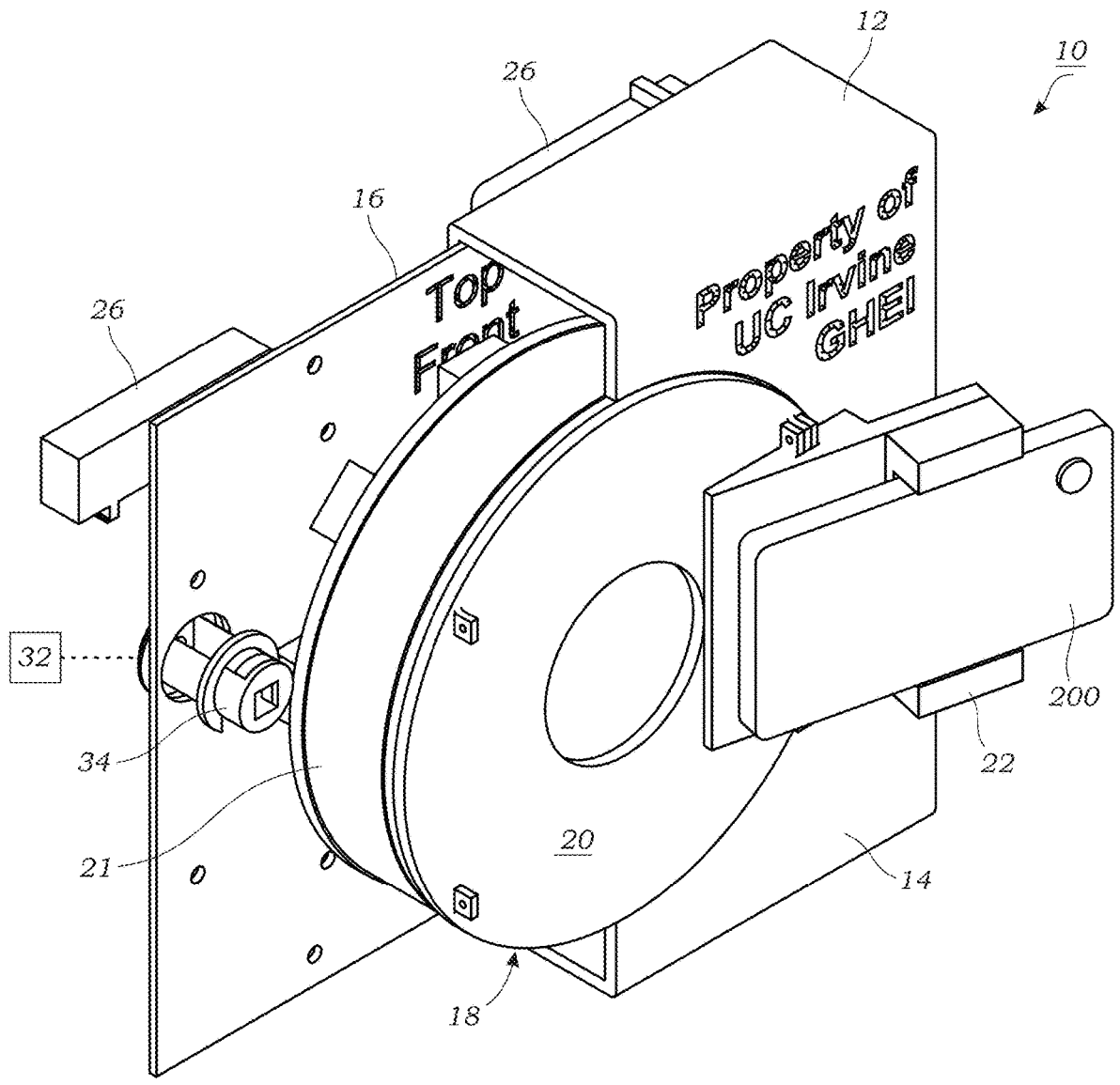
FIG. 1A illustrates a front perspective view of the universal actuator with a portion of the housing removed.

FIGS. 1A, 1B, 2A-2C, and 3 illustrates a universal actuator 10 according to one embodiment. The actuator 10 includes a housing 12 that includes a front side 14 and an opposing rear side 16. The front side 14 includes one or more actuators 18 that impart directional movement of an imaging device 200 secured thereto. The one or more actuators 18 may move in the horizontal direction, vertical direction, and/or rotational direction. In the illustrated embodiment, the one or more actuators 18 moves in a rotational direction. The imaging device 200 is mounted directly or indirectly on the one or more actuators 18. In some embodiments, the imaging device 200 may include a camera such as a camera that is found on a Smartphone or other portable electronic device as is illustrated in FIGS. 1A and 2A-2C. In other embodiments, the imaging device 200 may also include an imaging probe (e.g., ultrasound probe). In one particular application, the imaging device 200 is an imaging probe that is used to image the human eye.

Figure 1B:
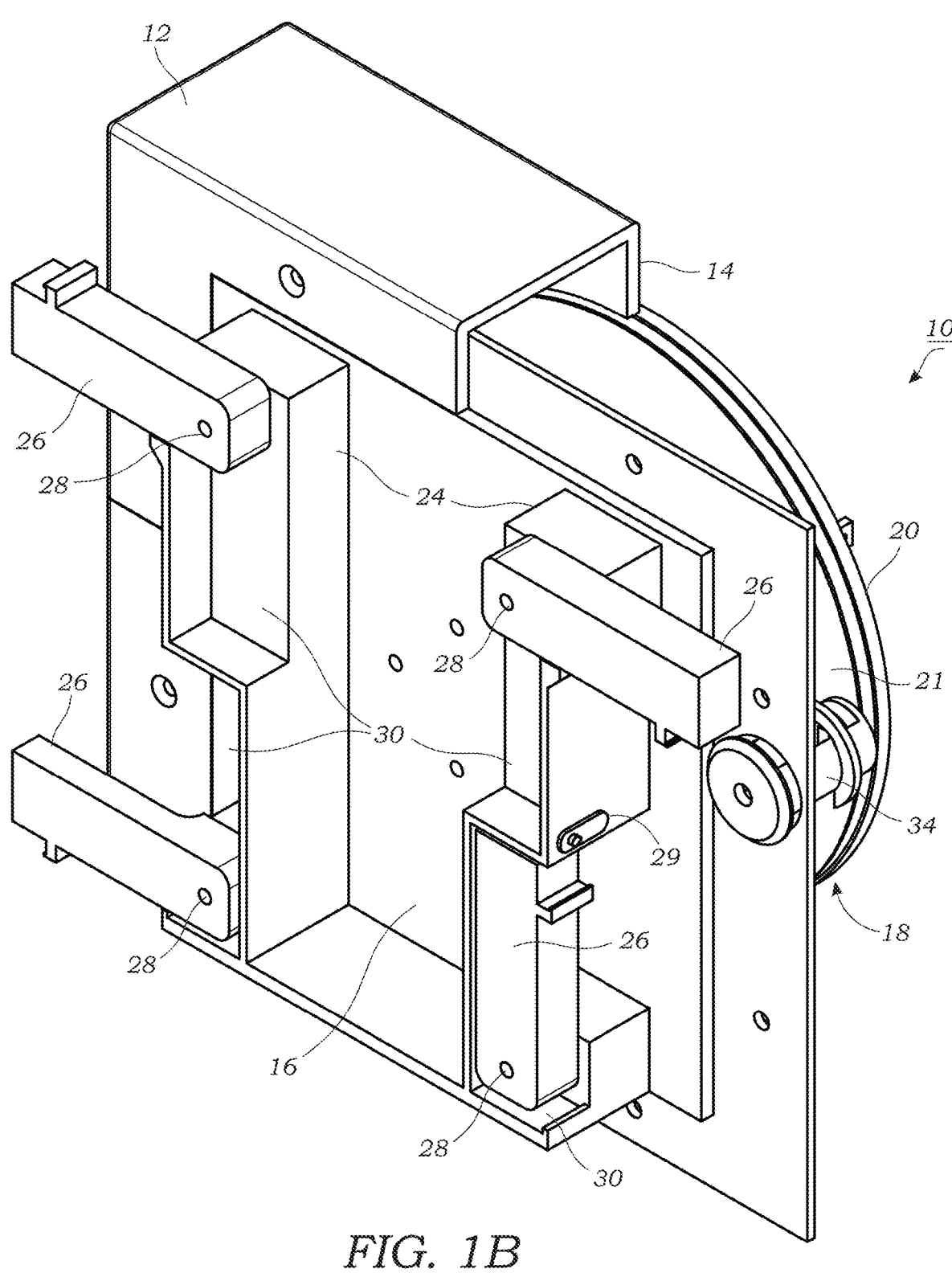
FIG. 1B illustrates a back perspective view of the universal actuator with a portion of the housing removed.
Figures 2A, 2B, 2C:
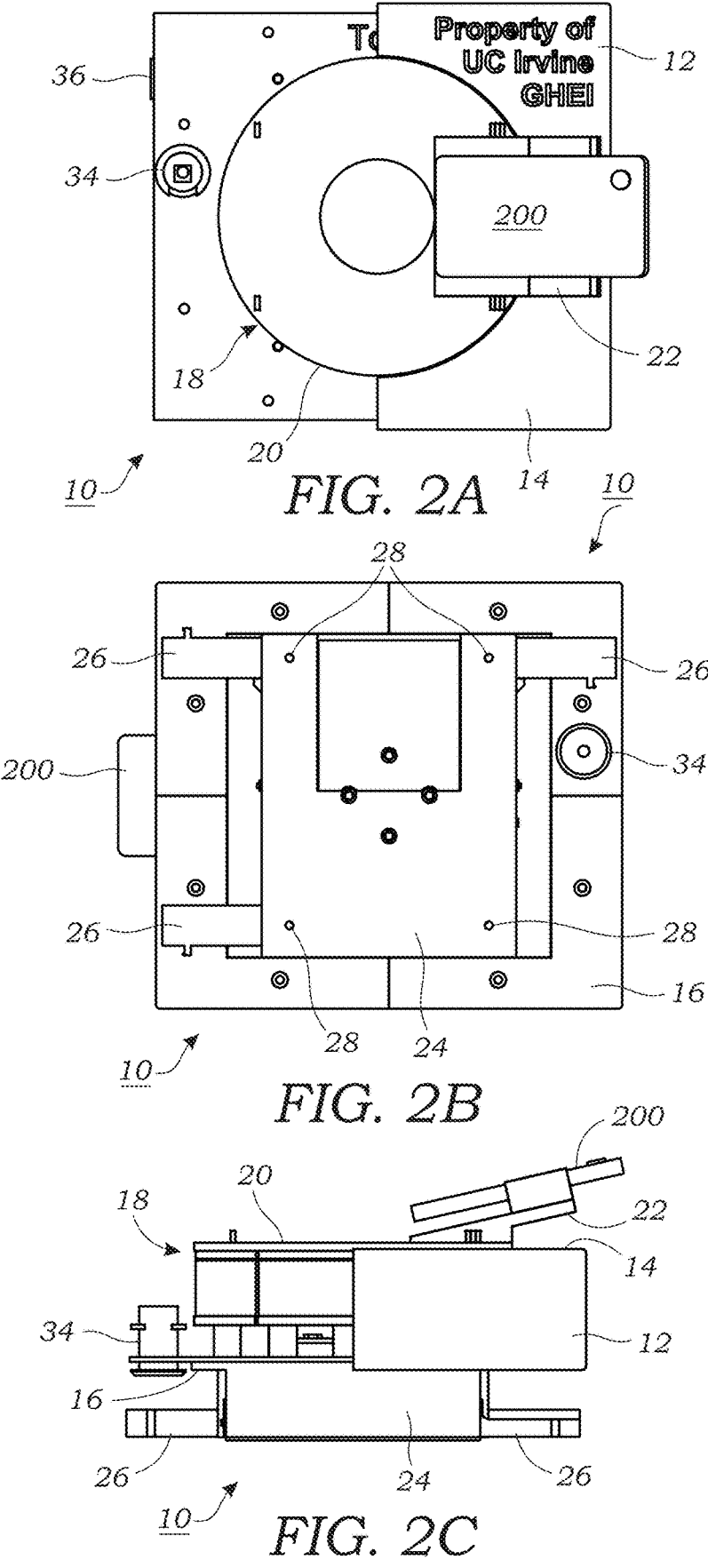
FIGS. 2A-2C illustrates front (FIG. 2A), back (FIG. 2B), left-side, and bottom (FIG. 2C) views of the universal actuator according to one embodiment.

The housing 12 contains the electronics for operating the one or more actuators 18. In one embodiment, as illustrated in FIGS. 1A, 1B, 2A, 2C, the one or more actuators 18 includes a rotatable platform 20 that imparts rotational motion to the imaging device 200 mounted thereon. The rotatable platform 20 includes a mount 22 on which the imaging device 200 is mounted. A rotary motor 21 (FIGS. 1A, 1B) in the housing 12 drives the rotation of the platform 20 that is secured thereto. The housing 12 may be made from any number of materials (e.g., plastic or other polymers, metal, wood, etc.). The mount 22, in one embodiment, is located on a radially-outward portion of the rotatable platform 20 and may be angled so that that camera of the imaging device 200 is also positioned at an angle relative to the object to be scanned as is best illustrated in FIGS. 1A and 2C. The object to be scanned or imaged may include, for example, the subject's face, orbital features, or the subject's eye(s).

Figure 3:
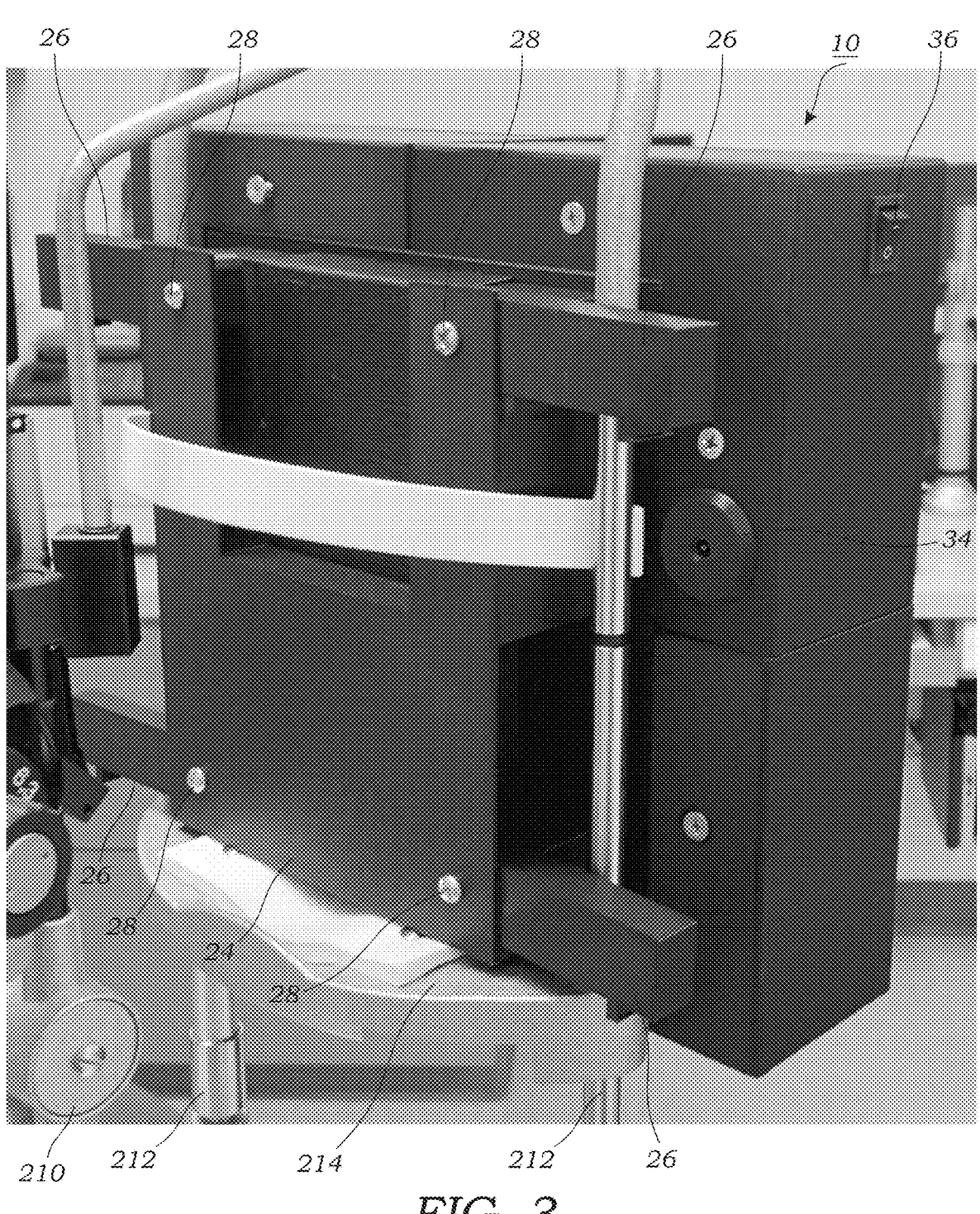
FIG. 3 illustrates a photograph the universal actuator mounted on the chin rest of a slit lamp microscope. This view illustrates the interface including the rear extension and fins or tabs that are used to lock the universal actuator to the chin support and side supports.

The imaging device 200 may include a structured-light camera or it may include a conventional camera. The rear side 16 of the housing 12 includes an interface that allows the actuator 18 to be removably mounted on the stand of the slit lamp microscope 210 as seen in FIG. 3. The interface includes a rear extension 24 that includes a plurality of rotatable fins or tabs 26 that extend outwardly from the rear extension 24. In one embodiment, the fins or tabs 26 are rotatable about a pin or fastener 28. The fins or tabs 26 are securely stored in the actuator housing 12 within respective storage recesses 30 when not deployed (best seen in FIG. 1B). In this regard, the fins or tabs 26 are nested within the housing 12 when not in use. An optional latch 29 may be used for each fin or tab 26 as seen in FIG. 1B to securely lock the same in the respective storage recess 30. After the universal actuator 18 is mounted to the chin rest 214 of stand of the slit lamp microscope 210, the fins or tabs 26 are rotated to secure the actuator 18 to the stand of the slit lamp microscope 210 (FIG. 3). For example, the fins or tabs 26 may be secured to the vertical side bars 212 that support the chin rest 214 of the stand of the slit lamp microscope 210.

In one embodiment, the four fins or tabs 26 are located at the four corners of the rear extension 24. The fins or tabs 26 may have a length of around 8 cm measured from the pivot point at the pin or fastener 28 to the end of the fin or tab 26. The two upper and two lower fins or tabs 26 may be located at around 12.5 cm from one another (measured at the point of rotation) in the horizontal direction. Vertical separation between the upper fins or tabs 26 and the lower fins or tabs is around 17 cm in one embodiment. Of course, the various dimensions of the vertical side bars 212 and the chin rest 214 may vary with different makes and models of slit lamp microscopes 210. However, the length of the fins or tabs 26 can accommodate different widths between the vertical side bars 212. In the illustrated embodiment, the housing 12 may have a height of around 27 cm and a width of around 29 cm. The total depth of the housing 12 (including the rear extension 24) is around 12 cm. Looking at the rear extension 24 only, it has a depth of around 4.5 cm.

The universal actuator 10 is powered using a power source 32. The power source 32 may be a battery or a conventional power adapter plugged into a wall outlet to provide power for the universal actuator 10. The illustrated embodiment uses a 13V DC power splitter 34 coupled to the on/off switch 36 and the rotary motor 21 that is mechanically coupled to the rotatable platform 20. The rotatable platform 20 may be operated by manual actuation or it may automatically rotate for a specified period of rotation(s) or time in response to a program or a set of automated instructions. In one embodiment, a remote control (not shown) may be used with the universal actuator 10 that enables a user to start and stop the rotation of the platform 20 or start and stop a pre-programed rotational routine. For example, a pre-programmed routine may include one full rotation of the rotatable platform 20.

Figure 4:
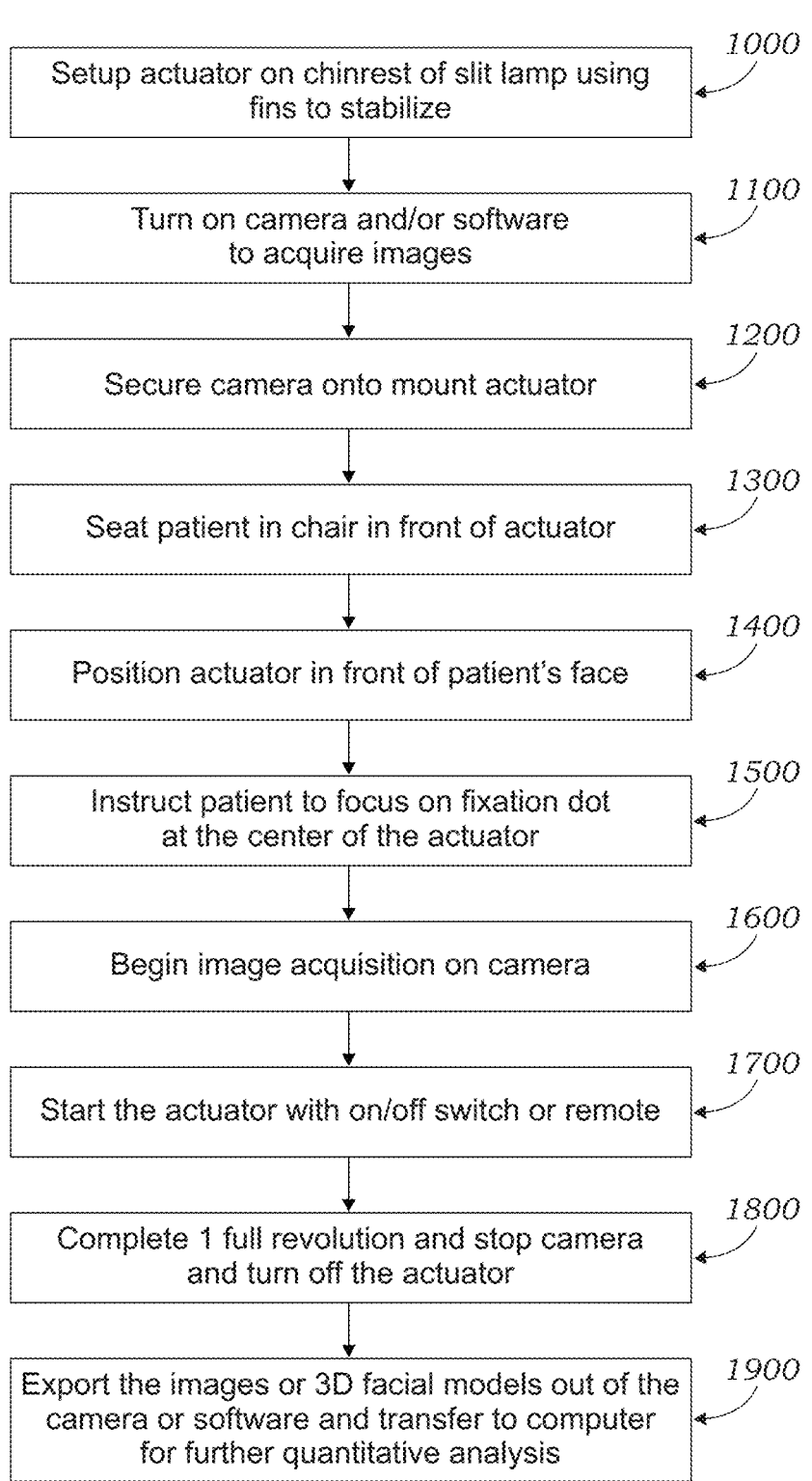
FIG. 4 illustrates an exemplary workflow of using the universal actuator of FIGS. 1A, 1B, 2A-2C, and 3.
Figure 5:
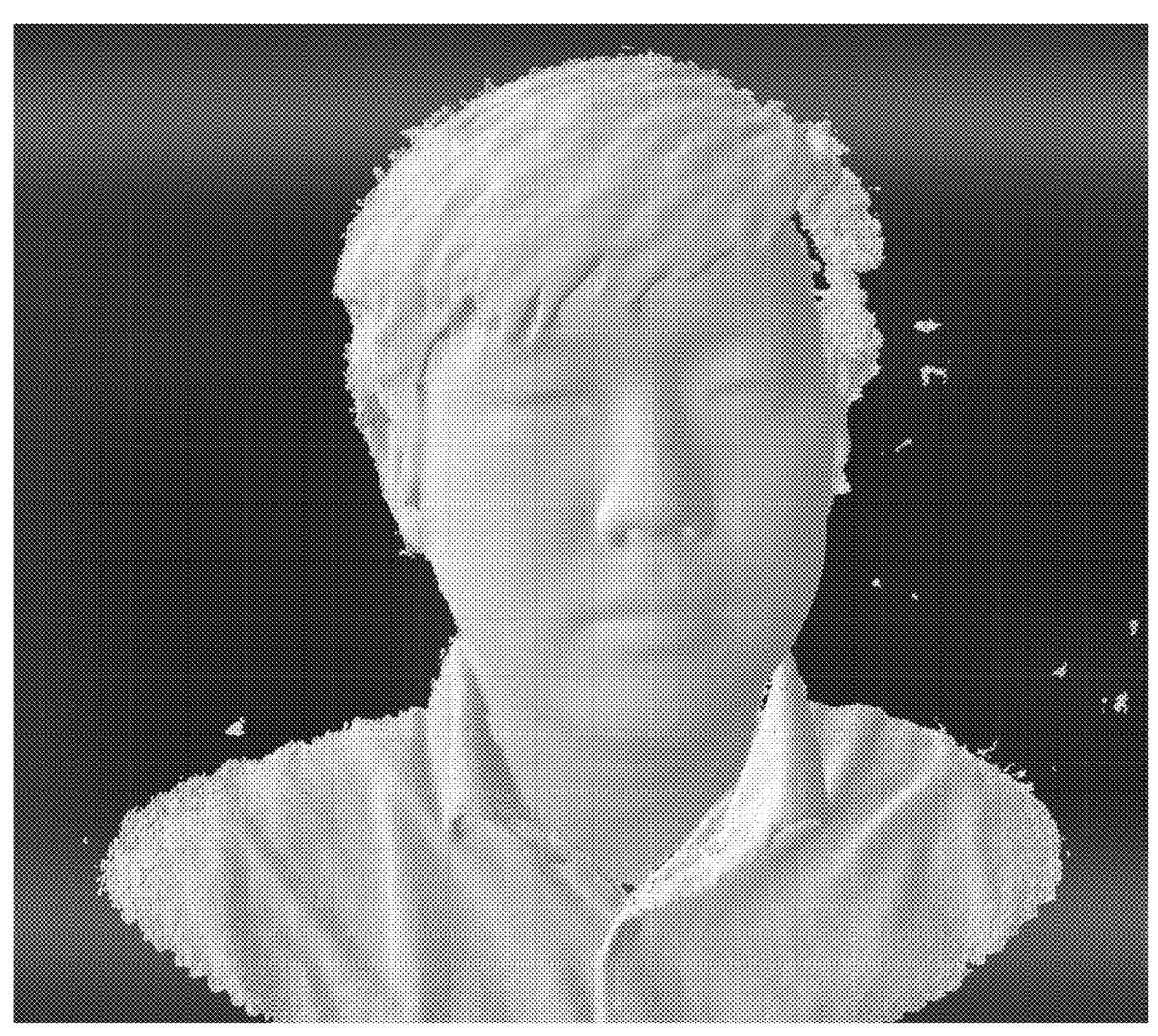
FIG. 5 illustrates an exemplary 3D face scan using the universal actuator of FIGS. 1A, 1B, 2A-2C, and 3.

The universal actuator for 10 moving an imaging device 200 of FIGS. 1A, 1B, 2A-2C is used in conjunction with a slit lamp microscope 210 illustrated in FIG. 3. FIG. 4 illustrates an exemplary workflow for the universal actuator 10. The universal actuator 10 is mounted on the chin rest 214 of the slit lamp microscope 210 (operation 1000). Specifically, the bottom surface of the rear extension 24 of the housing 12 rests on the chin rest 214 and the four fins or tabs 26 are rotated out of their respective storage recesses 30 and contact the vertical side bars 212 holding the chin rest 214 of the slit lamp microscope 210. The height of the universal actuator 10 on the slit lamp microscope 210 is adjusted to place the one or more actuators 18 around the level of the object to be scanned (e.g., face of a subject). For the rotational embodiment, the center of rotation of the rotatable platform 20 is placed in front of the subject's face. With reference to operation 1100 of FIG. 4, the imaging device 200 (e.g., Smartphone) which is in the mount 22 is turned on and includes software or an application "app" that acquires a series of images or a movie as the imaging device 200 is rotated on the platform 20. The imaging device 200 is mounted to the platform 20 via the mount 22 as seen in operation 1200. The patient is seated in a chair (operation 1300) and the universal actuator 10 is positioned in front of the patient's face (operation 1400). The patient is instructed to focus on a fixation dot at the center of the universal actuator 10 as seen in operation 1400. Image acquisition then begins as seen in operation 1600. For example, the shutter button of the imaging device 200 is pressed to begin the imaging. Movement of the rotatable platform 20 is then initiated as seen in operation 1700. This may be initiated manually (e.g., using a switch) or with a remote control. The platform 20 rotates at a substantially uniform rotational speed in response to a motor contained in the universal actuator 10 that drives the rotatable platform 20. A series of images or a movie of an object (e.g., subject's face) is obtained as the imaging device 200 is rotated on the platform 20. The scan is completed after one full rotation of the imaging device 200 as seen in operation 1800 of FIG. 4, although the scan may also be completed in less than a full rotation or more than a single rotation in other embodiments. The images or movie may be obtained using an imaging device 200 such as a structured-light camera of a portable electronic device or the images or movie may be acquired using a conventional camera of a portable electronic device. Software in the imaging device 200 or the portable electronic device then assembles the acquired 2D images to generate a 3D image, representation, or model of the object that is scanned. An example of this software is Scandy Pro (www.scandy.co New Orleans, LA) although other software programs or applications may be used. In one embodiment, the object that is scanned is a person's face, although it should be appreciated that other objects may be imaged. FIG. 5 illustrates an example of a 3D face scan output. The images or 3D facial models may be exported to another computer or computing device for further quantitative analysis as seen in operation 1900 of FIG. 4. Alternatively, the 3D images, representations, or models may also be created on a separate computing device and not necessarily on the imaging device 200 or camera.

It should be understood that in other embodiments, the universal actuator 10 may include different actuators 18 that impart lateral and/or vertical motion to the imaging device 200. For example, the universal actuator 10 may include one or more moveable stages that allow for the imaging device 10 to move horizontally and/or vertically. For example, one stage may be used for horizontal motion while another stage is used for vertical movement. In addition, the type of imaging device 200 that is secured to the one or more actuators 18 may vary. For example, the imaging device 200 may be an imaging probe for imaging of the eye such as an ultrasound-based imaging probe.

Universal Actuator—Pivoting Scan #1

Figures 6A, 6B, 6C, 6D:
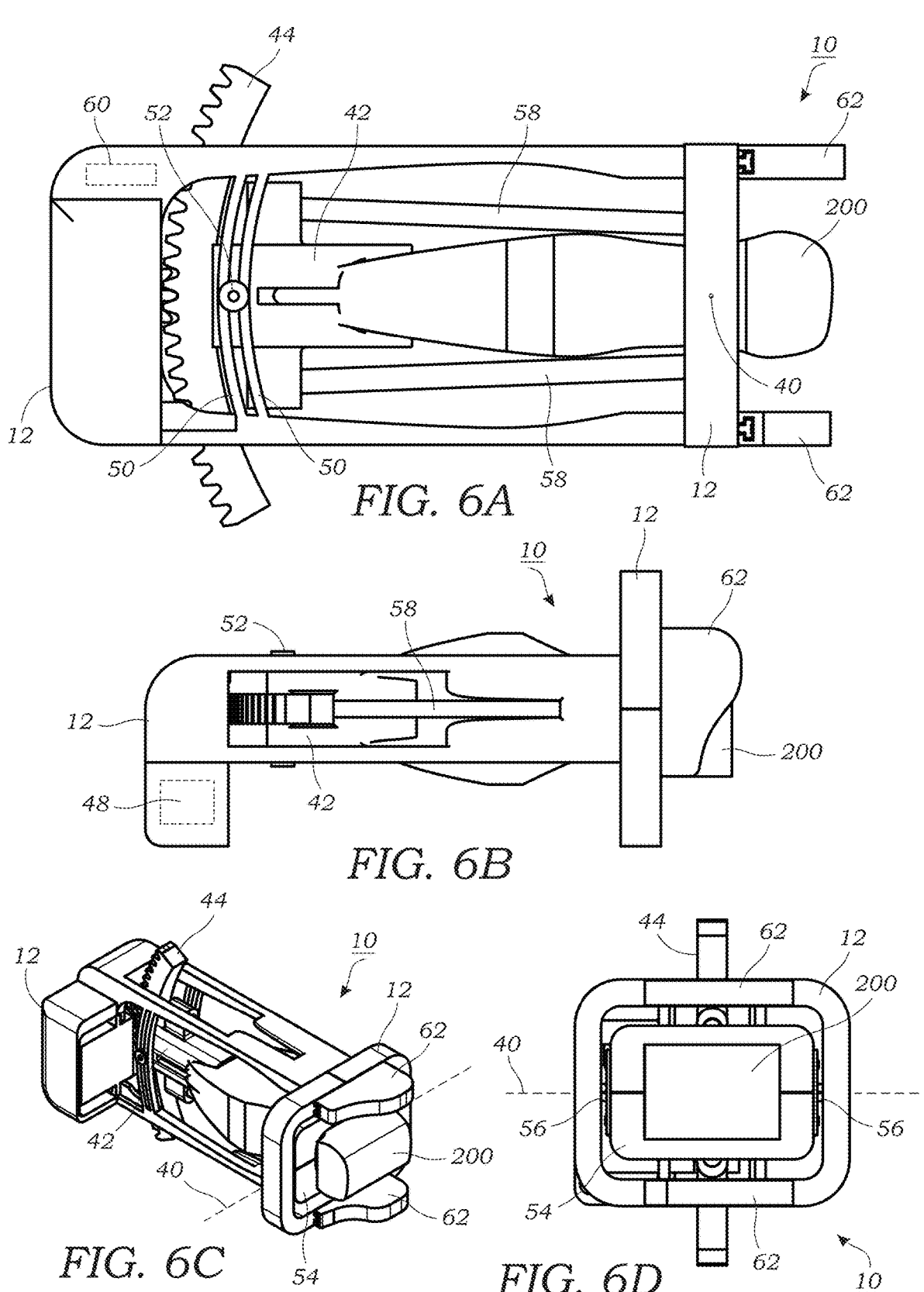
FIG. 6A illustrates a side view of another embodiment of a universal actuator. In this embodiment, rotational (pivoting) motion is imparted to an imaging device such as a probe contained therein.
FIG. 6B illustrates a top view of the universal actuator of FIG. 6A.
FIG. 6C illustrates a perspective view of the universal actuator of FIG. 6A.
FIG. 6D illustrates a front view of the universal actuator of FIG. 6A.
Figure 6E:
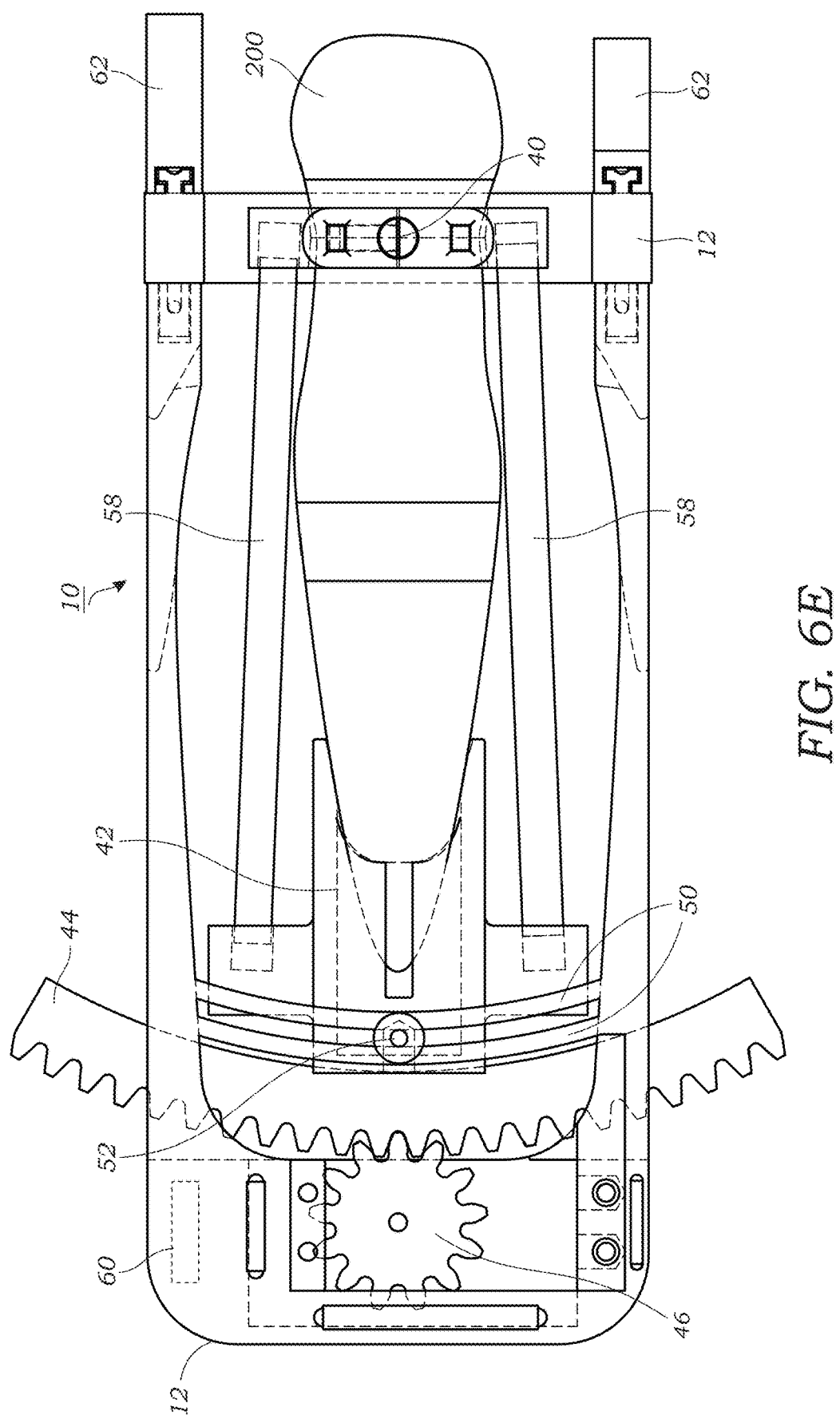
FIG. 6E illustrates a top view of the universal actuator of FIG. 6A showing the pinion gear engaging with the curved rack.

FIGS. 6A-6E illustrate another embodiment of a universal actuator device 10. In this embodiment, the universal actuator device 10 houses an imaging device 200 such as an ultrasound probe and enables pivoting of the probe about a pivot axis 40 (seen in FIGS. 6A, 6C, 6D, 6E). This pivot axis 40 is oriented generally orthogonal to the long axis of the probe 200 and thus the motion of the probe 200 is a pivoting or rotational movement along a plane (e.g., horizontal plane) about the pivot axis 40. In some embodiments, the pivot axis 40 extends through the longitudinal axis of the imaging device 200 (i.e., it passes through the physical imaging device 200 as it does in the embodiment of FIGS. 6A-6E). In other embodiments, however, the pivot axis 40 may extend distally of the imaging device 200. For example, in the context of an ultrasound imaging probe for the eyes, the pivot axis 40 may extend through the eye. The universal actuator device 10 may be hand-held, or it may be mountable on another device such as the slit lamp microscope 210. The universal actuator 10, in this embodiment, has a probe receiver 42 that receives the proximal (back) end of the probe 200. This probe receiver 42 may be a receptacle that receives the proximal end of the probe 200 or the probe receiver 42 may include a sleeve that grips the exterior surface of the probe 200. In one implementation, the back or proximal end of the probe 200 may be pressed into the probe receiver 42. The probe receiver 42 is coupled to a curved rack 44 that engages with pinion gear 46 as seen in FIG. 6E mounted in the universal actuator 10 that is powered by a servo motor 48 as seen in FIG. 6B. The servo motor 48 and pinion gear 46 may be contained in a housing 12 of the universal actuator 10. Rotation of the pinion gear moves the curved rack 44 and the probe receiver 42 (and probe 200 contained therein) in an arc. A pair of guide rails or slots 50 (FIGS. 6A and 6E) may be provided in the housing 12 that interface with a pin 52 on the probe receiver 42 to aid in moving the proximal probe receiver along an arc. Rotation of the servo motor 48 in a first direction moves probe receiver 42 and probe 200 in one direction along the arc while rotation of the servo motor 48 in a second, opposing direction moves the probe receiver 42 and probe 200 in the opposing direction along the arc. A pivot collar 54 engages with the distal end of the probe 200. The pivot collar 54 may be dimensioned to accommodate a particular make or model of the ultrasound probe 200 or it may accommodate different ultrasound probe types. The pivot collar 54 may be made in two pieces and surrounds the probe 200. The pivot collar 54 may include flexible contact surfaces that allow the pivot collar 54 to accommodate different geometries and sizes of the probe 200. The pivot collar 54 includes respective pins 56 on opposing sides that engage with the housing 12. The pivot collar 54 is secured to the probe receiver 42/curved rack 44 via support rods 58. This ensures that movement of the curved rack 44 translates into well-defined pivoting of the pivot collar 54 and the probe 200 contained therein (i.e., so the ultrasound probe 200 and the curved rack 44 move as one component). The probe receiver 42 and pivot collar 54 may be contained in the housing 12, which in some embodiments may include an enclosure or handle. The actuator device 10 may be hand-held or the actuator device 10 may be mounted on a slit lamp microscope 210 using the using the universal interface disclosed herein.

Figure 20A:
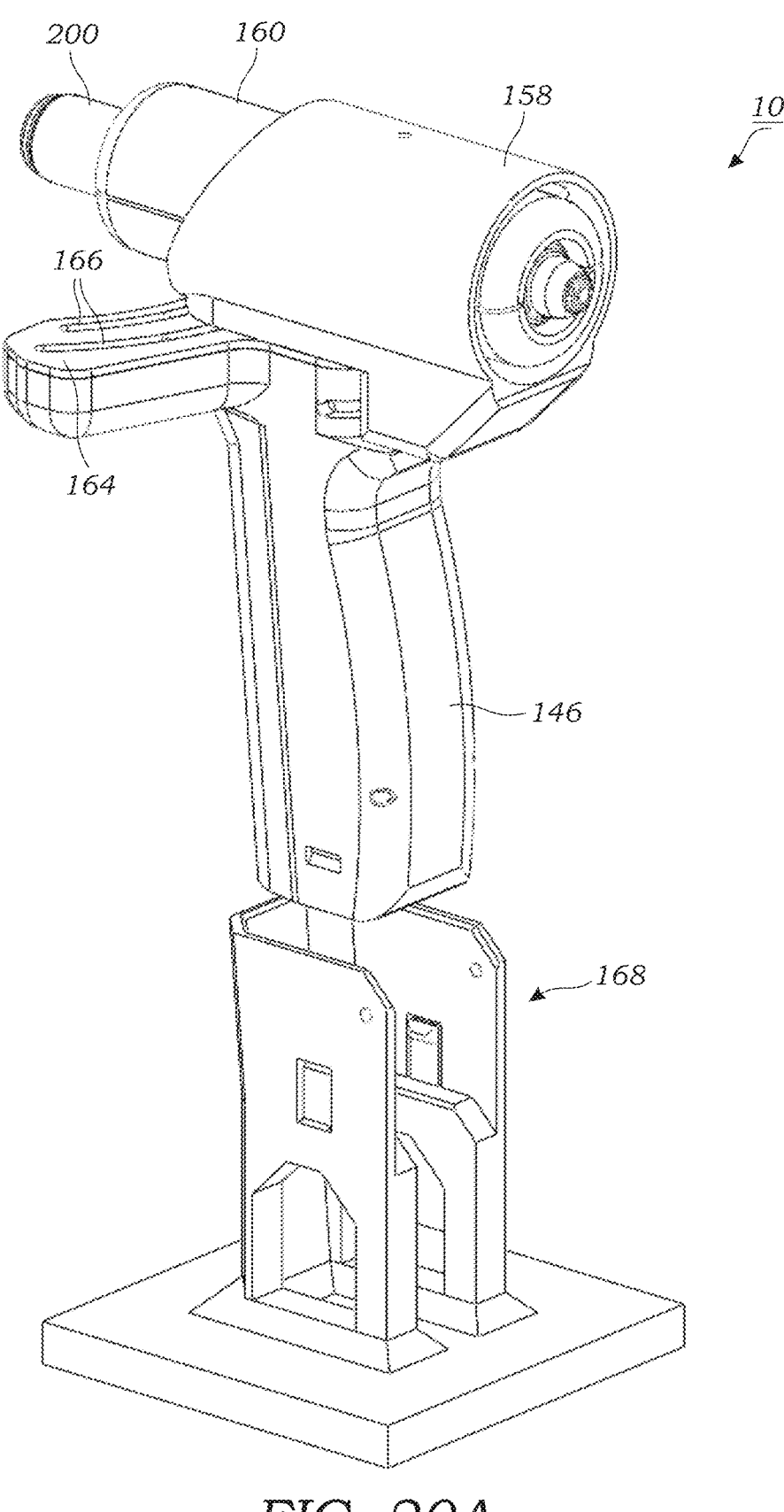
FIG. 20A illustrates a hand-held embodiment of a universal actuator. The universal actuator pivots a probe (e.g., ultrasound probe) along an arc and also provides for rotational (axial) scanning.

In this embodiment, the pivot collar 54 and the probe 200 contained therein pivots back and forth about the pivot axis 40 defined at the location where the respective pins 56 of the pivot collar 54 engage with the housing 12. The distal end of the probe 200 or probe head includes the imaging element that is used to capture image(s) of the object. The probe 200 may be, for example, an ultrasound probe. A controller 60 (e.g., microcontroller) (FIGS. 6A and 6E) may be used to control the servo motor 48 which in turn controls the movement of the pinion gear 46 and thus the curved rack 44 and the proximal end of the probe 200. The controller 60 may be integrated into a housing of the universal actuator 10 such as handle 146 in the embodiment illustrated in FIGS. 20A-20C. The controller 60 may be programmable so that the probe tracks pre-defined movement. This may be, for example, oscillating or back-and-forth pivoting of the probe 200. The curved rack 44 can be moved back-and-forth along an arc while the distal end of the probe 200 (end of probe 200 in pivot collar 54) pivots about the pivot axis 40 defined by the pivot collar 54. The probe receiver 42 and the pivot collar 54 may be designed to accommodate any number of makes and models of probes 200 and probe types. The sweep angle may be adjustable but is typically several tens of degrees (e.g., between 10° and 40°). The universal actuator 10 may include surface contact pads (e.g., foam or other soft material) that are mounted on extensions 62 located at the distal end to aid in positioning the universal actuator 10 onto the face of the subject. Alternatively, the extensions 62 themselves may act as the surface contact pads.

Figure 7:
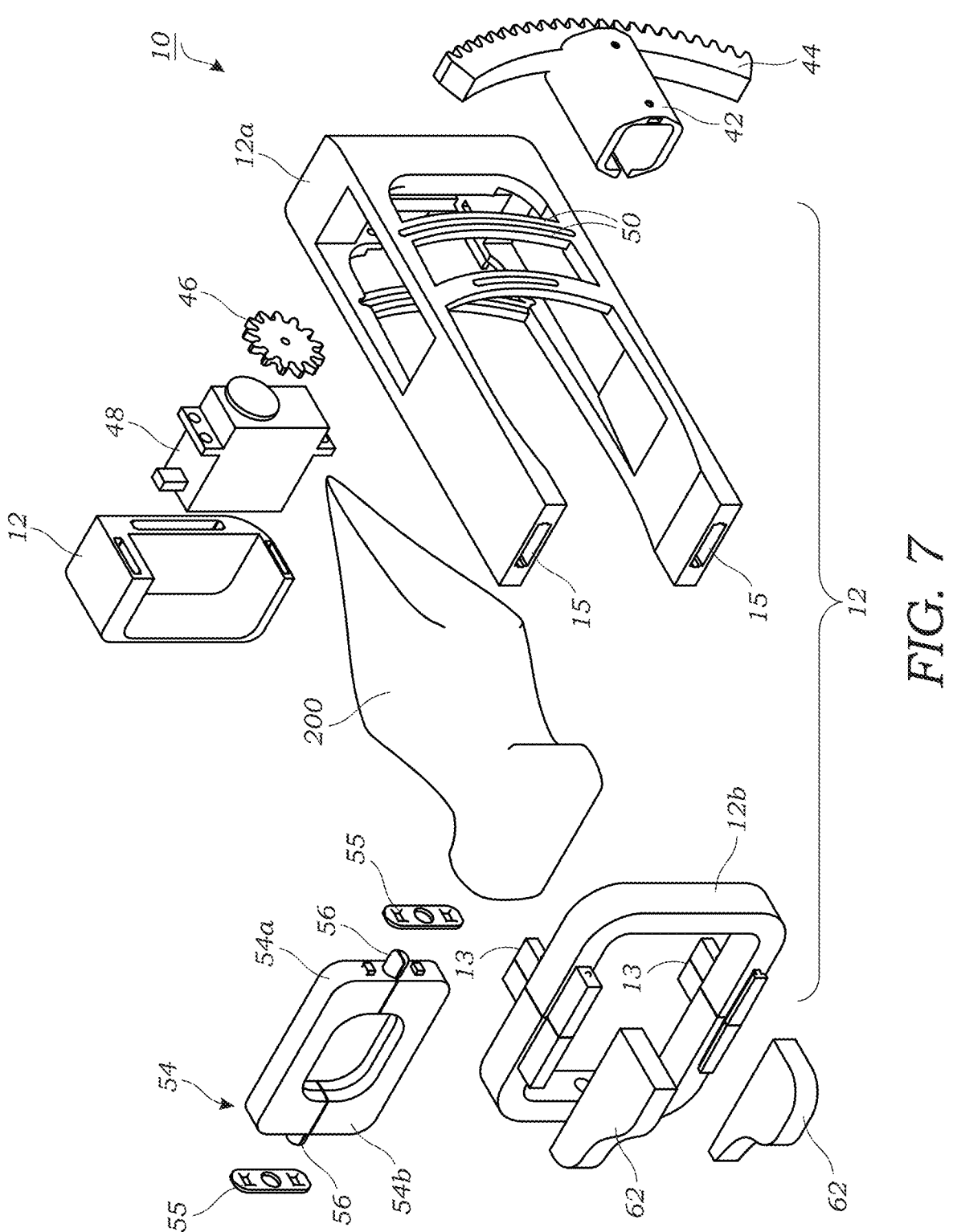
FIG. 7 illustrates another embodiment of a universal actuator that is used to rotate (pivot) an imaging device such as a probe.

FIG. 7 illustrates another version of the actuator 10 that provides pivoting motion to a probe 200. The housing 12 includes a proximal portion 12a and a distal portion 12b. The distal portion 12b includes tabs 13 that insert into holes 15 in the proximal portion 12a. The pivoting collar 54 is made from a first half 54a and a second half 54b. The two halves 54a, 54b are secured to one another via respective clips 55 that have holes that receive the pins 56. The pins 56 interface with the distal portion 12b of the housing and allow for pivoting motion of the probe 200 that is contained therein.

One use of the universal actuator 10 and the ultrasound probe 200 is to take 2D ultrasound images of the eye of the subject and generate a 3D volumetric representation of the eye and the surrounding tissues. Here, the universal actuator 10 is positioned adjacent to the eye of the subject such that distal end of the probe 200 contacts the corneal surface of the eye and the servo motor 48 is activated to move the curved rack 44 and thus cause the probe 200 to pivot about the pivot axis 40. The images of the eye may be captured a computing device that is linked with the probe 200. This may include, for example, a portable electronic device using image capture software. An example is the Butterfly image capture application although other applications may be used. A 3D model of the eye is generated from the 2D images of the eye along with the orientation information for each image that has been taken. Positional information of the probe 200 is registered for each image that is obtained which is then used by software to generate the 3D model of the eye. It should be appreciated that this embodiment may be hand-held and used manually or it may be mounted on a fixture or other device, for example, the slit lamp microscope 210.

Figure 8:
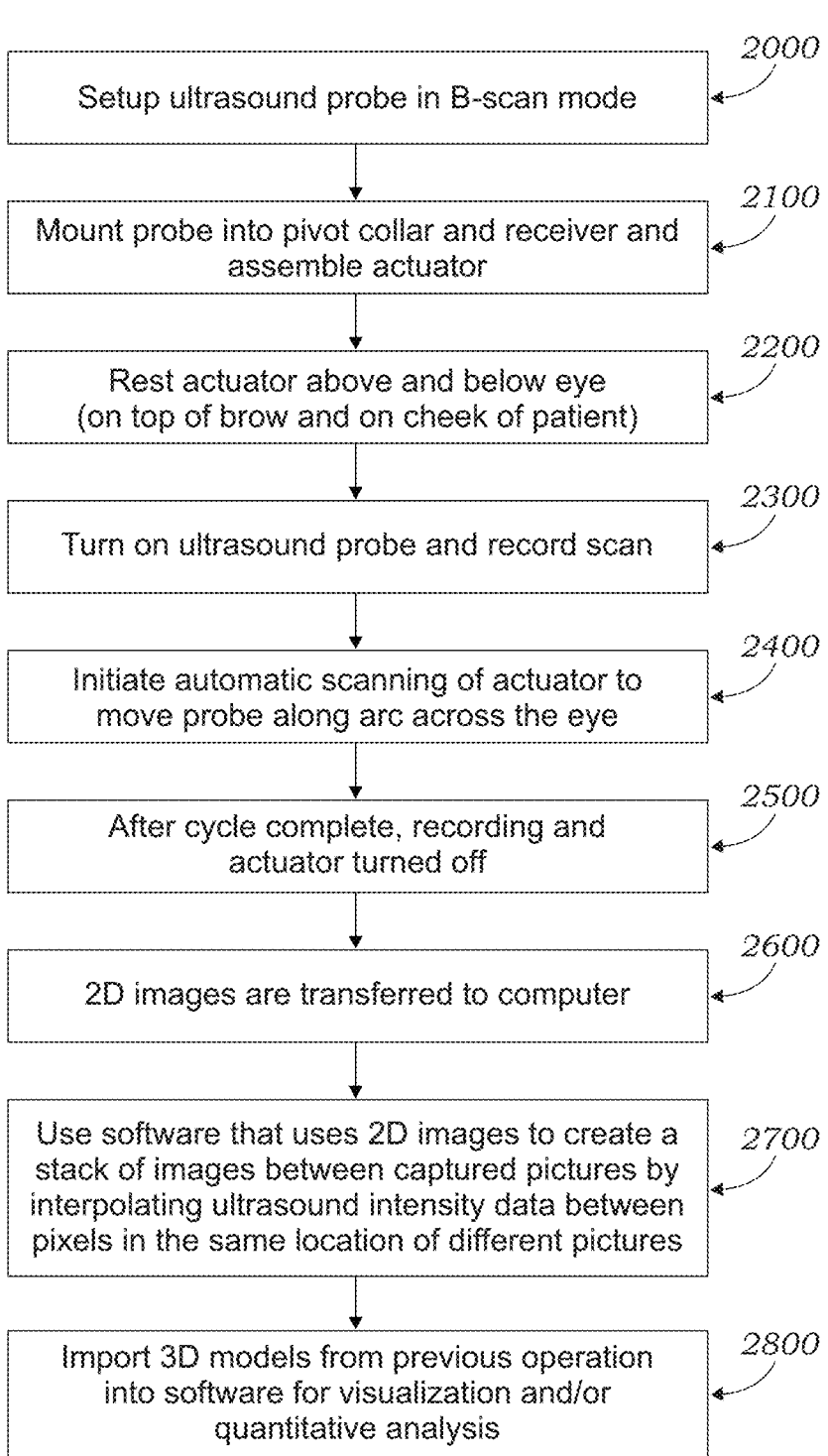
FIG. 8 illustrates an exemplary workflow of using the universal actuator of FIGS. 6A-6E and 7.
Figure 9A:
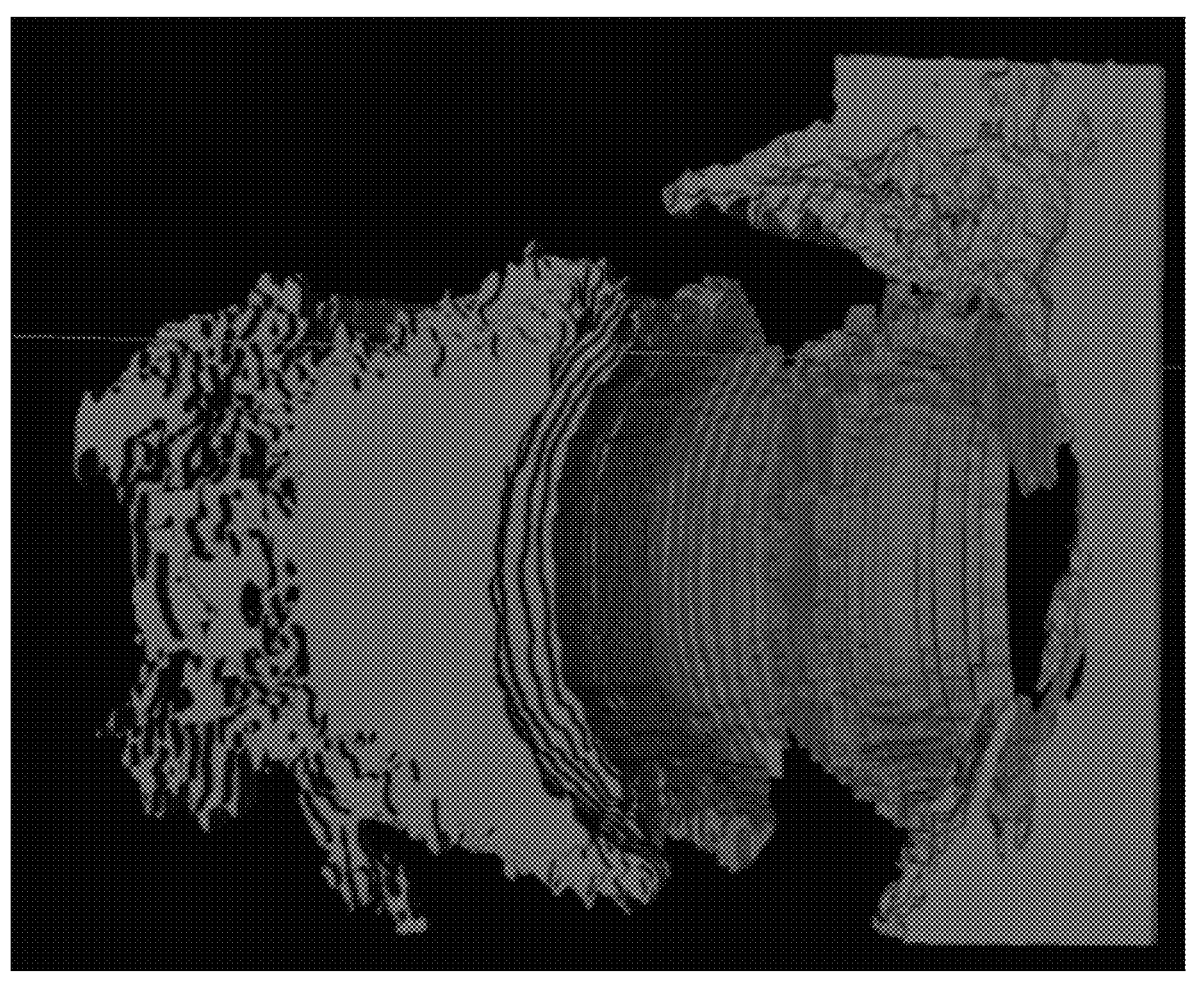
FIG. 9A illustrates a screen shot of a video/movie of a scan of the eye using the universal actuator. The scan shows the soft-tissue structures such as the retina-choroid complex at the back of the eye.

FIG. 8 illustrates an exemplary workflow for using the universal actuator 10. Here the ultrasound probe 200 of choice is setup (operation 2000) and mounted in the pivot collar 54 and the probe receiver 42 of the universal actuator 10 (operation 2100). The universal actuator 10 is rested above the eye on top of the brow of the patient as well as bellow the eye on the check bone (operation 2200). The scanning head of the probe 200 is in light contact with the surface of the eye. The ultrasound probe 200 is turned on to begin recording the scans (operation 2300). The universal actuator 10 is turned on to move the ultrasound probe 200 along an arc across the eye (operation 2400). After the automated program completes 1 cycle, recording is stopped along with the movement of the universal actuator 10 (operation 2500). Note that multiple cycles across the eye may be performed in some cases. The obtained 2D images are exported or otherwise transferred to an associated computing device (operation 2600). The 2D images is loaded into a custom MATLAB program executed on the computing device to create an image stack (operation 2700). An image processing software is used to interpolate or "fill in" ultrasound intensity data between pixels in the same location of different 2D images to create the 3D model. The model may be imported into software such as, for example ITK-Snap, a free, open-source software application, for visualization and quantitative analysis (operation 2800). FIG. 9A illustrates a screen shot of a video/movie of a scan of the eye using the universal actuator 10. The scan shows the soft-tissue structures such as the retina-choroid complex at the back of the eye.

Universal Actuator—Three Axis+Rotation

In another embodiment, with reference to FIGS. 10-18 a universal actuator device 10 is provided that mounts on the base of a slit lamp microscope 210 and provides for movement of an imaging probe 200 in the horizontal direction and vertical direction along with rotational movement of the imaging probe 200. The universal actuator device 10 includes a mount 70 that allows the universal actuator 10 to be mounted on a standard slit lamp microscope 210. The slit lamp microscope 210 is rotated out of the way 90 degrees so the universal actuator 10 can be secured to the slit lamp microscope 210 via the mount 70. The mount 70 is affixed with a screw to the rotating column. Vertical motion is provided by the scissor platform 72 secured to the mount 70 that is driven by a stepper motor 74 to move the platform 72 up and down. A linear actuator 76 is secured atop the top/platform of the scissor platform 72 to provide for horizontal linear motion using a stepper motor 78 that moves a platform adapter 80 back-and-forth in a horizontal direction. The linear actuator 76 includes an outer stationary adapter 81 that is attached to the scissor platform 72. The moveable adapter 80 within the stationary adapter is coupled to a stepper motor 78 that moves the moveable adapter 80 in a linear direction. The moveable adapter 80 of the linear actuator 76 is secured to a top or platform 82 that holds a rotational actuator 84 that provides rotational movement to the imaging probe 200.

Figure 12:
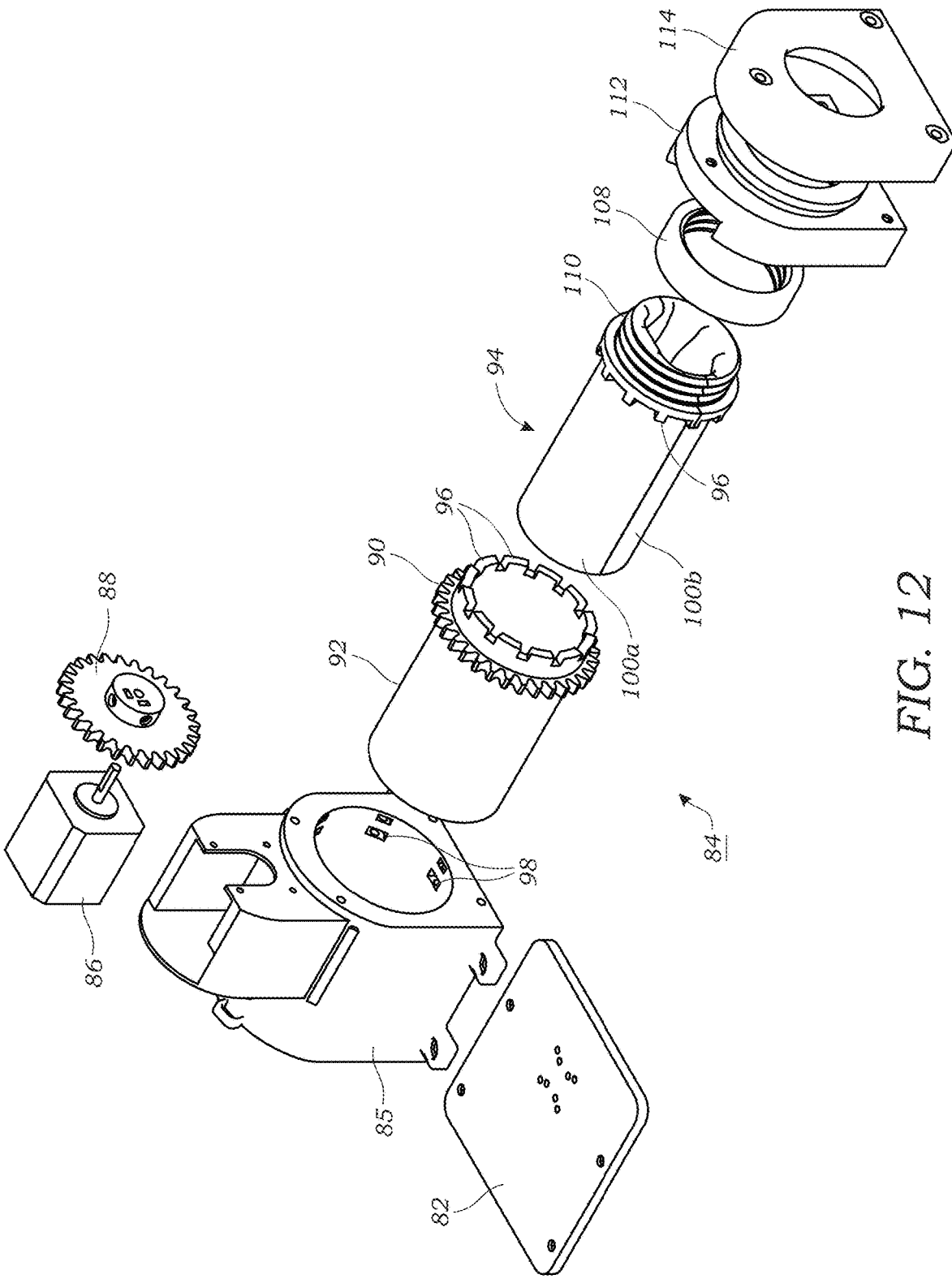
FIG. 12 illustrates an exploded view of the rotational actuator of the embodiment of FIG. 10.
Figure 13:
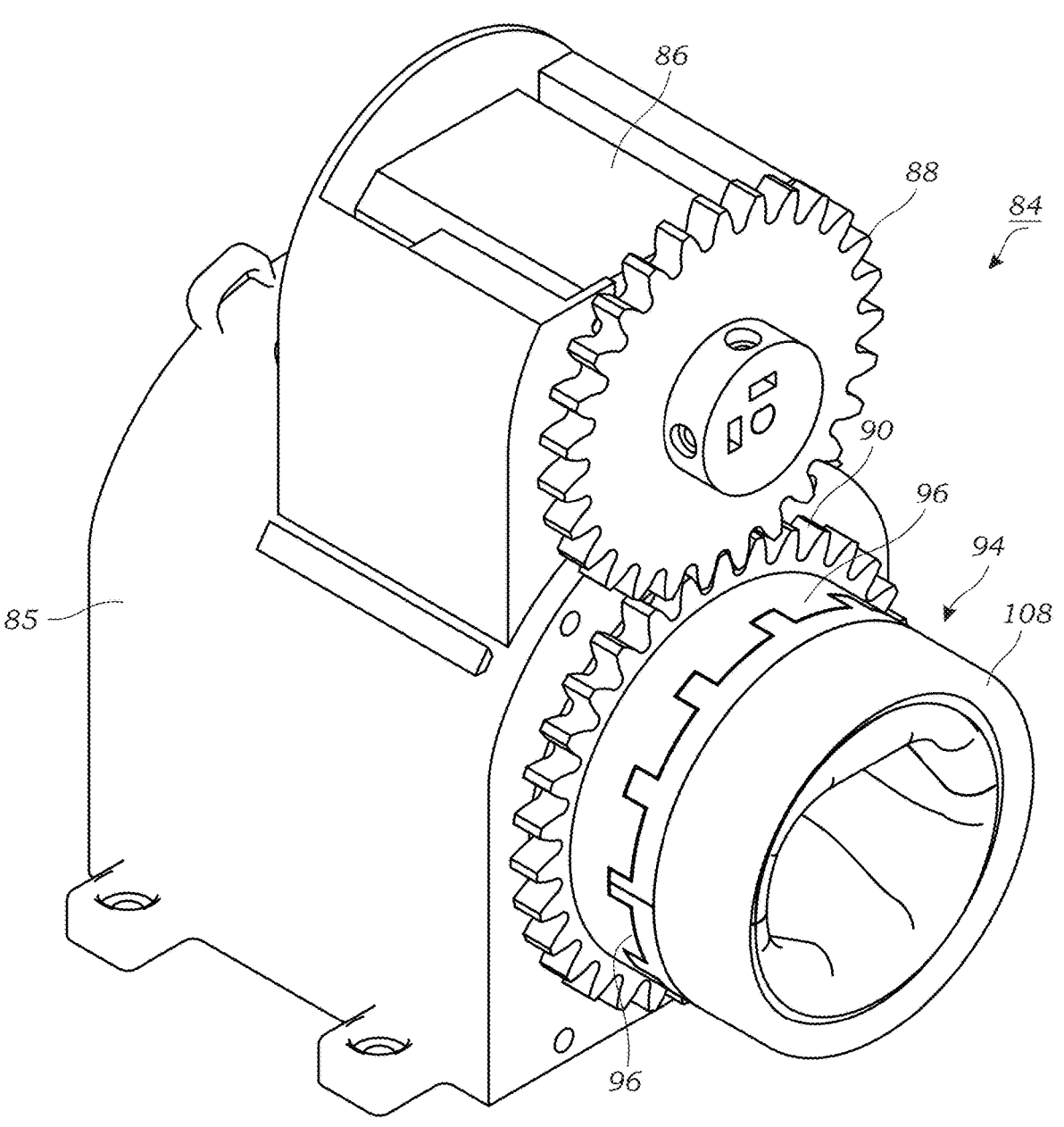
FIG. 13 illustrates the rotational actuator of FIG. 12.
Figure 14:
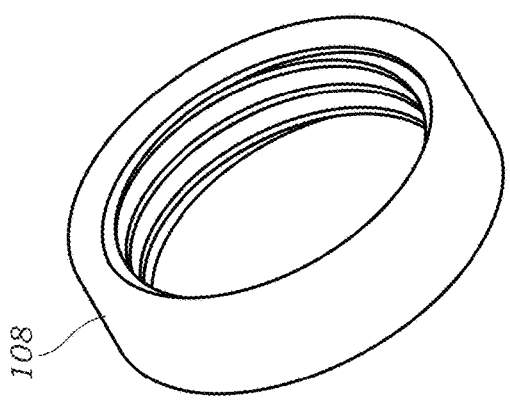
FIG. 14 illustrates the probe adapter halves and locking ring.
Figure 14:
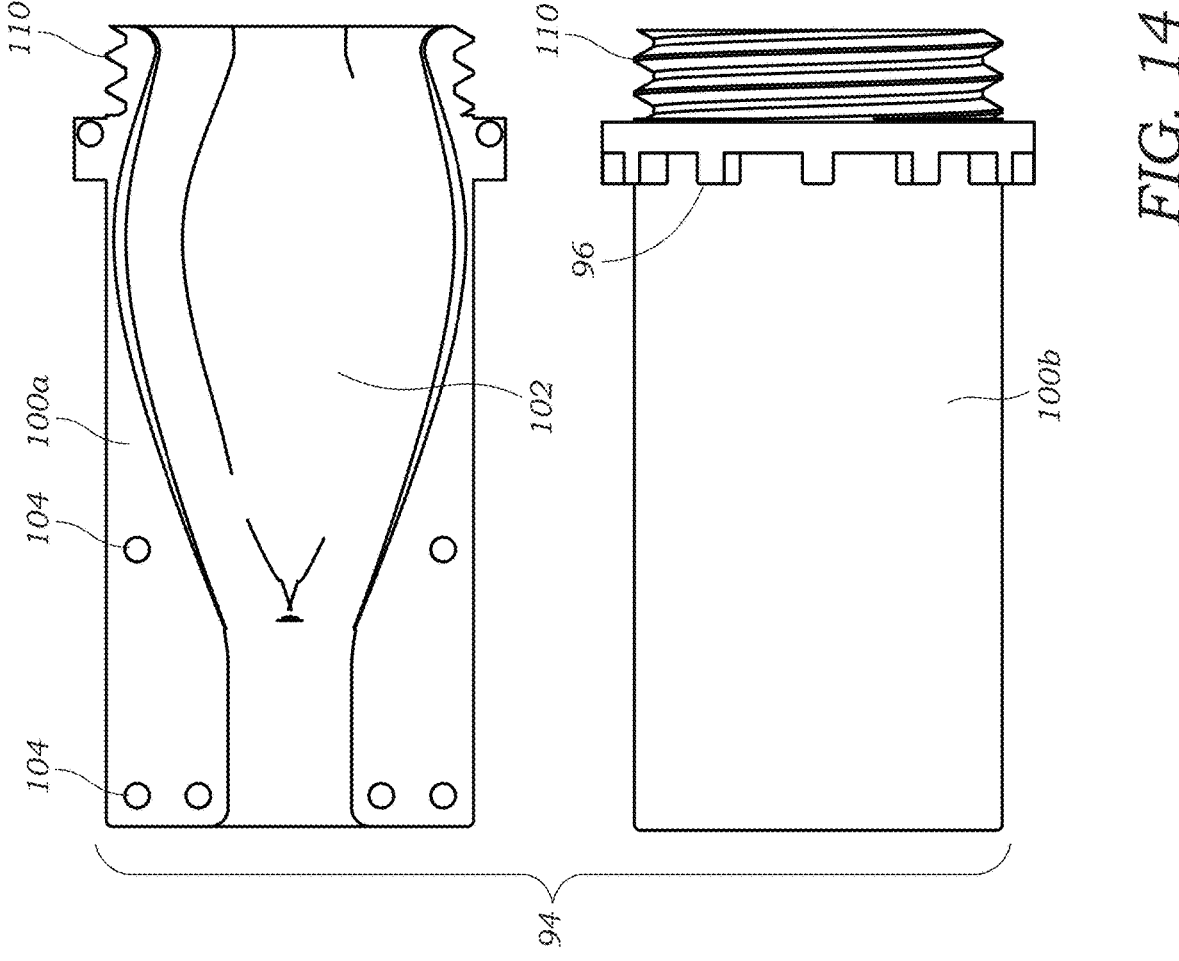

With reference to FIGS. 12-14, the rotational actuator 84, which is secured to the platform 82 of the moveable adapter 80, includes a stepper motor 86 that powers a drive gear 88. The drive gear 88 engages with the teeth 90 of a universal rotation sleeve 92 that extends into the body 85 of the rotational actuator 84 and rotates in response to the actuation of the stepper motor 86. The universal rotation sleeve 92 receives a probe adapter 94 that is dimensioned to hold the imaging probe 200 (e.g., ultrasound probe). The probe adapter 94 extends into the lumen of the universal rotation sleeve 92 and is locked relatively thereto using keyed surfaces 96 located on the universal rotation sleeve 92 and the probe adapter 94. The keyed surfaces 96 may include interlocking teeth that are used to transfer torque from the universal rotation sleeve 92 to the probe adapter 94. As seen in FIG. 12, the inside bore of the body 85 rotational actuator 84 may contain a plurality of ball bearings 98 that contact with the outer surface of the universal rotational sleeve 92.

The ball bearings 98 reduce friction during rotation of the universal rotational sleeve 92 in the rotational actuator 84.

Figure 10:
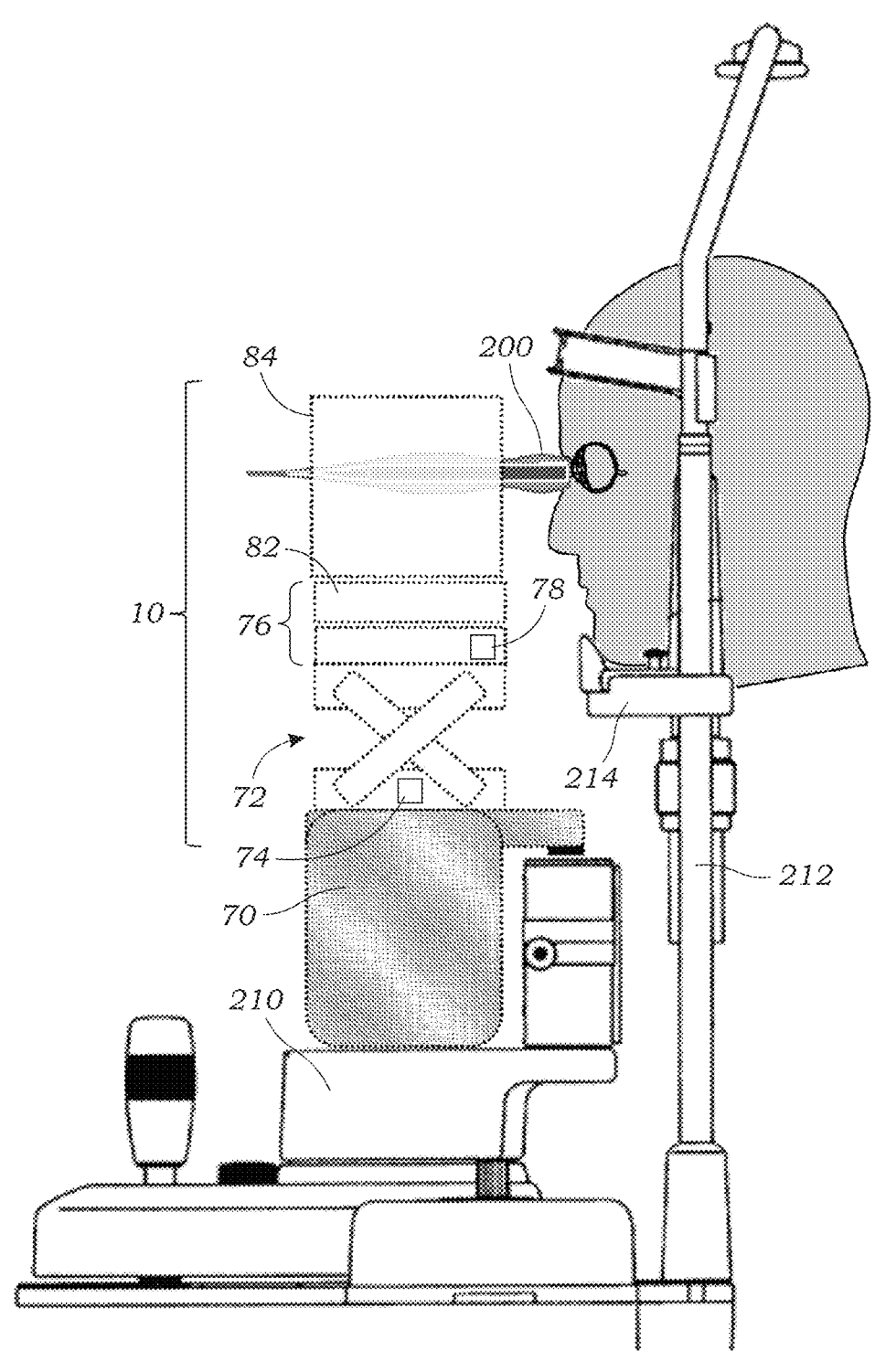
FIG. 10 illustrates another embodiment of a universal actuator. The universal actuator is illustrated mounted to a slit lamp microscope and moves a probe in the vertical, horizontal, and rotational (axial rotation) directions.
Figure 11:
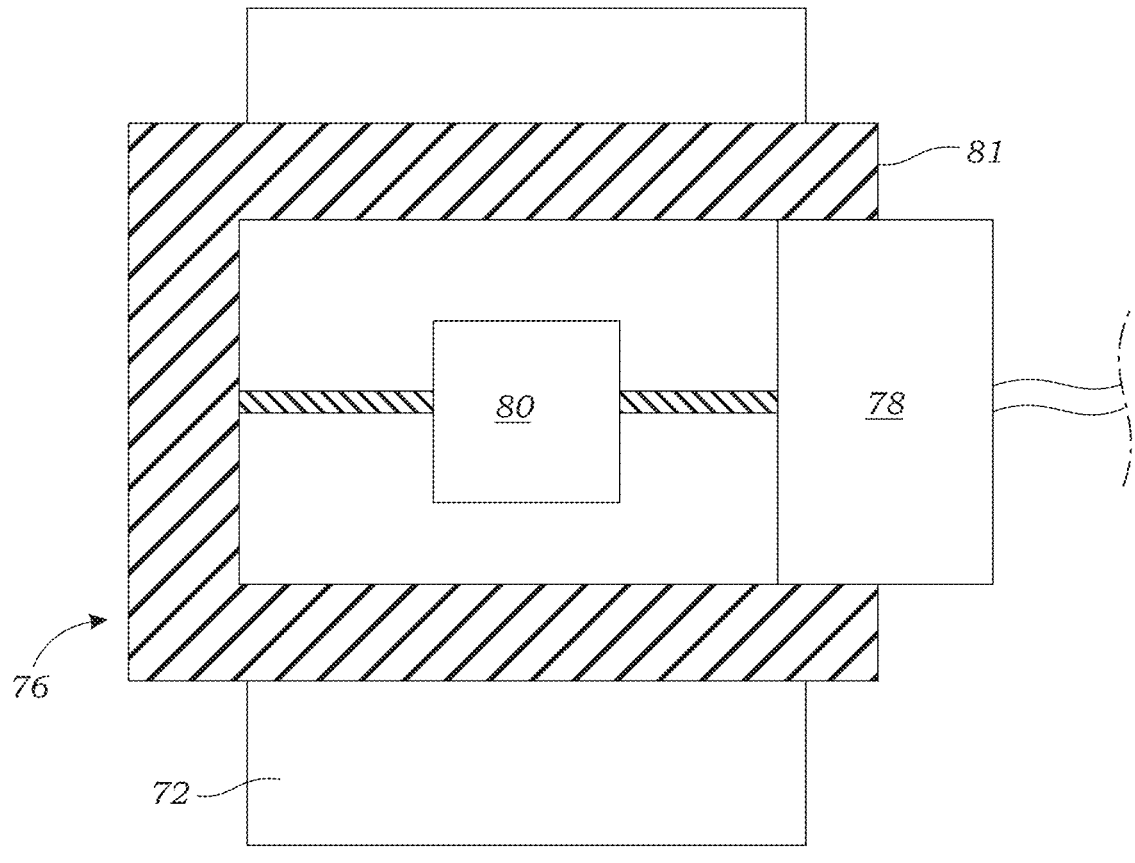
FIG. 11 illustrates the horizontal axis linear actuator components.

The probe adapter 94 receives an imaging probe 200 inside thereof as seen in FIG. 10. The probe adapter 94 may be sized and dimensioned to accommodate a wide variety of makes, models, and types of imaging probes 200. The probe adapter 94 is formed as two mating halves 100a, 100b as best seen in FIG. 14. A recess or cutout profile 102 in each half 100a, 100b is shaped and dimensioned to accommodate a particular make or model of the imaging probe 200. In this way, a tight fit is formed between the imaging probe 200 and the probe adapter 94 when assembled that prevents any unwanted movement. Studs 104 and corresponding holes (now shown) formed in the respective halves 100a, 100b ensures precise mating of surfaces to encapsulate the imaging probe 100. In this example, an adapter or locking ring 108 engages with threaded surfaces 110 on the probe adapter halves 100a, 100b to mechanically secure the two halves 100a, 100b to one another. With reference to FIG. 12, end caps 112, 114 ensure that the universal rotational sleeve 92 and the probe adapter 94 remain in the rotational actuator 84. Specifically, the end cap 112 ensures that the universal rotational sleeve 92 remains within the body 85 of the rotational actuator 84 while end cap 114 ensures that the probe adapter 94 remains inside of universal rotational sleeve 92. With the imaging probe 200 mounted in the probe adapter 94, the assembly is inserted into the universal rotation sleeve 92. Any wires coupled to the probe may extend through the rotational actuator 84 via a hole or port formed in the body 85 (not illustrated).

Figure 15:
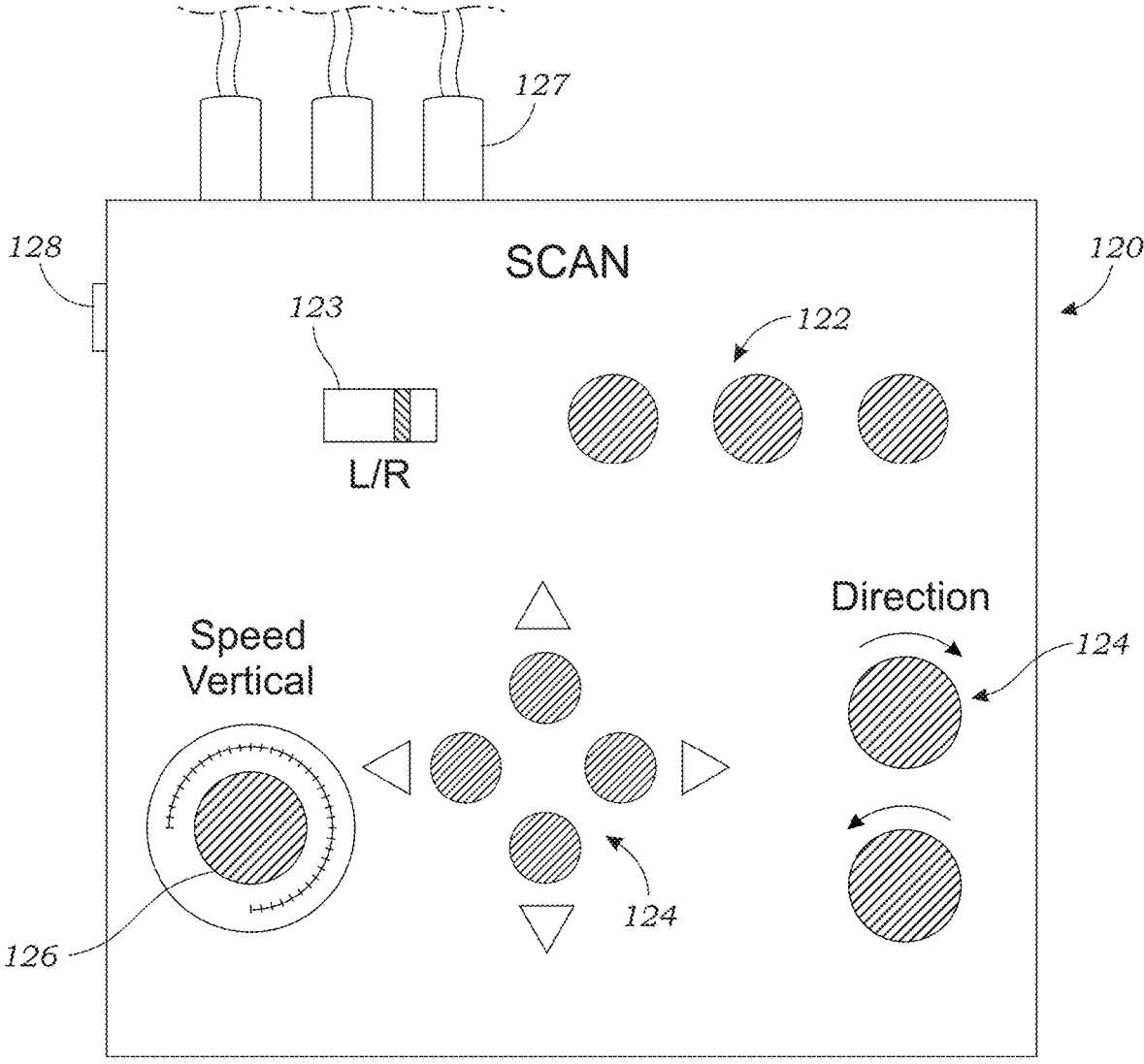
FIG. 15 illustrates a top view of the control box according to one embodiment.

The universal actuator device 10 is connected to a control box 120 (FIG. 15) that controls the movement of the imaging probe 200 by the various actuators (e.g., scissor platform 72, linear actuator 76, and the rotational actuator 84). This includes movement in the horizontal and vertical directions as well as rotational movement. The control of the scans can be controlled by adjusting the respective directions and/or speeds of the stepper motors. Pre-programmed scan paths may also be stored in the control box 120 and used to scan along pre-defined directional profiles. This may include the order of scans, number of scans in each direction, direction(s) of scans, the speed of each scan, and the like. FIG. 15 illustrates buttons 122 used for pre-programed scans for rotational movement, vertical movement, and horizontal movement. A switch 123 is provided that dictates the initial direction of the pre-programmed scan paths. Buttons 124 are also provided for manual control of the stepper motors. A speed control dial 126 is also provided for manual control of the stepper motors. Cables 127 are connected to the control box 120 and connect to each of the respective motors (rotational, vertical, and horizontal). A power switch 128 is used to turn the control box 120 on/off.

Figure 16:
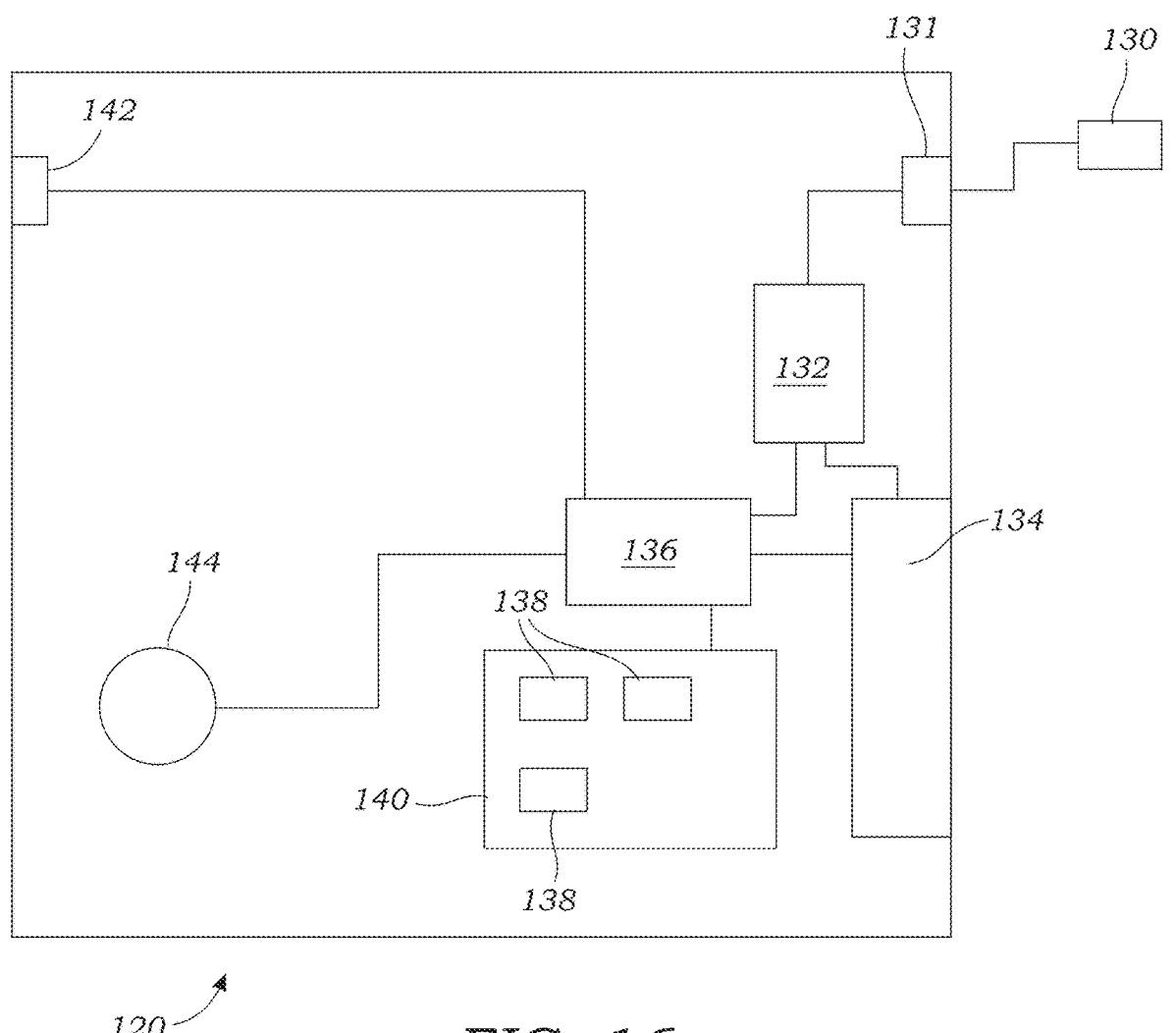
FIG. 16 schematically illustrates the internal electronics and circuitry of the control box.

FIG. 16 illustrates the internal electronics and circuitry of the control box 120. A 12V power supply 130 is used to power the control box 120. A 12V DC power switch 131 illuminates to indicate ON/OFF status. which is stepped down to 5V DC via a buck converter 132 to power a cooling fan 134 and Arduino microcontroller 136 and stepper motor drivers 138. Stepper motor drivers 138 are located on a PCB 140 disposed over the Adruino microcontroller 136 and connect to respective RS232 connectors at the back of the control box 120. The Arduino microcontroller 136 is located beneath the PCB 140 containing the stepper motor drivers/chips 138. A micro-USB port 142 is located in the control box 120 and allows changes to be uploaded to the micro-controller program or firmware. A 10 k Ohm potentiometer 144 is provided in the control box and is used as an 8-bit analog signal (between 0-255) sent to the Arduino micro-controller to variably control the speed of the stepper motors based on user preferences.

Figure 9B:
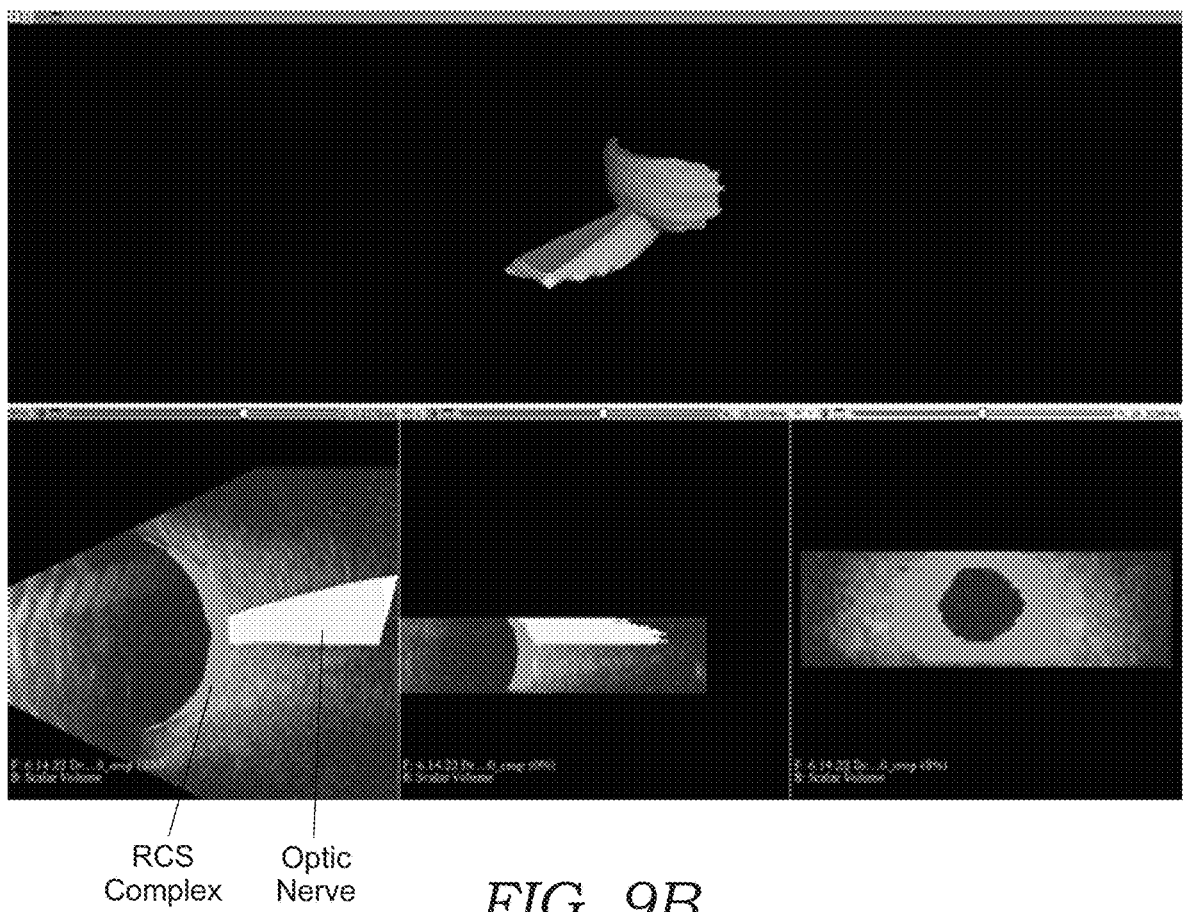
FIG. 9B illustrates an example of the 3D model of the rear or proximal region of the eye. The optic nerve and retina-choroid-sclera (RCS) complex can be seen which were manually segmented using Affinity Photo. Also illustrated below are various cross-sections.
Figure 18:
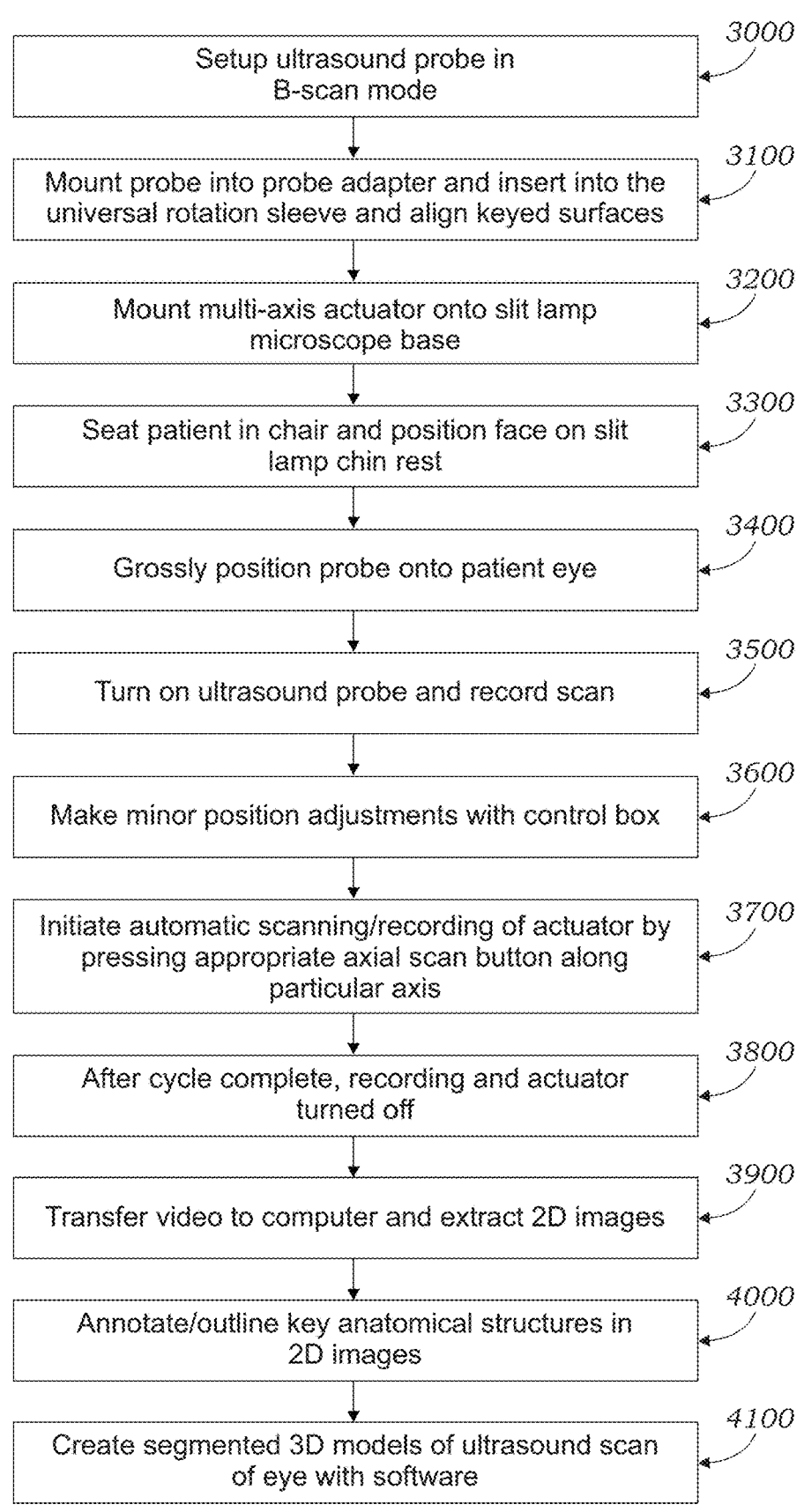
FIG. 18 illustrates an exemplary workflow of using the universal actuator of FIGS. 10-17.

To use the system of FIGS. 10-16, and with reference to FIG. 18, the imaging probe 200 of choice (e.g., ultrasound probe) is setup in B scan mode (operation 3000). The imaging probe 200 is mounted into the probe adapter 94 and secured with the adapter/locking ring 108. The probe adapter 94 is inserted into the universal rotation sleeve 92 and the teeth/keyed surfaces 96 are aligned (operation 3100). The cover of the rotational device is screwed on and the slit lamp microscope 210 opens (i.e., rotates 90°) to expose the rotating column. The universal actuator device 10 is then secured to the slit lamp microscope 210 using the mount 70 (operation 3200). The wires are connected to the control box 120 and the patient is seated in a chair to place their face in the slit lamp chin rest 214 (operation 3300). The imaging probe 200 is roughly positioned onto the patient's eye and the imaging probe 200 is turned on (operations 3400 and 3500). Minor adjustments to the position of the imaging probe 200 may be made using the control box 120 and the manual control buttons 124 (operation 3600). Recording of the images obtained from the imaging probe 200 is initiated and the axial scan button 122 is depressed to automate the imaging probe movement (operation 3700). A similar process is used for rotational scanning. After the cycle is complete the actuator 10 and probe 200 are turned off (operation 3800). The ultrasound movie/video or images are exported to a computer and image processing software automatically extracts 2D images form the movie/video (operation 3900). Key anatomical structures in the 2D ultrasound images may be annotated or outlined using a software program like Affinity Designer or Adobe Illustrator (operation 4000). In one embodiment, the 2D images are then loaded into an open-source software application such as 3D slicer to created segmented 3D models from the ultra-sound scans of the eye (operation 4100). FIG. 9B illustrates an example of the 3D model of the rear or proximal region of the eye. The optic nerve and retina-choroid-sclera (RCS) complex can be seen which were manually segmented using Affinity Photo. Also illustrated below are various cross-sections of the eye. Note that the images of the eye may be obtained using a combination of vertical motion, horizontal motion, and rotational motion. The imaging probe 200 may follow a pre-programmed set of instructions that are stored in the control box 120 on the microcontroller 136.

While the embodiment described above includes the linear actuator 76 disposed on the scissor platform 72, it should be appreciated that the scissor platform 72 or another vertical actuator may be mounted on the linear actuator 76. That is to say, the linear actuator 76 is located below on the scissor platform 72. This embodiment is illustrated in FIG. 17.

Figure 17:
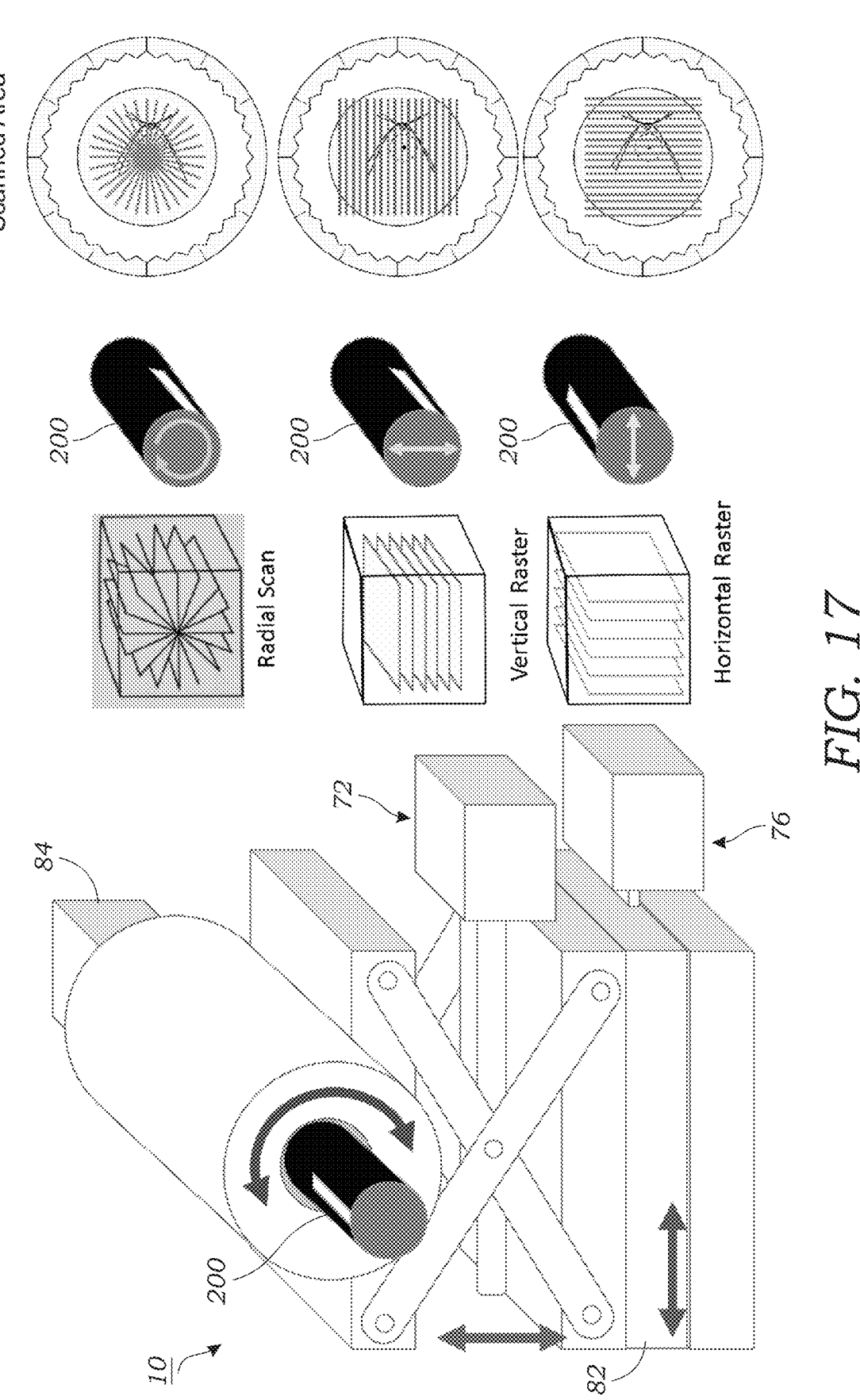
FIG. 17 schematically illustrates the multi-axis actuator of FIG. 10 along with the different probe scans achieved (radial scan, vertical raster, horizontal raster).
Figure 19:
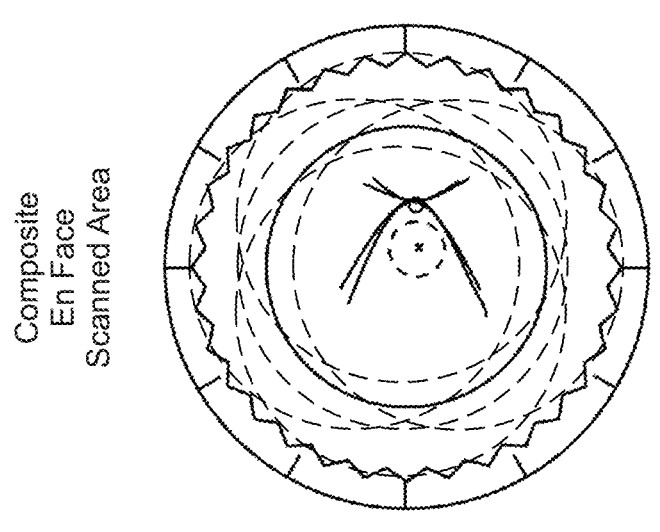
FIG. 19 illustrates how combining different images obtained at different rotational (pivot) angles of the imaging probe relative to the eye is able to create a large field-of-view. The dashed lines A, B, C illustrate the FOVs generated by the particular orientation (A, B, C) of the imaging probe.
Figure 19:
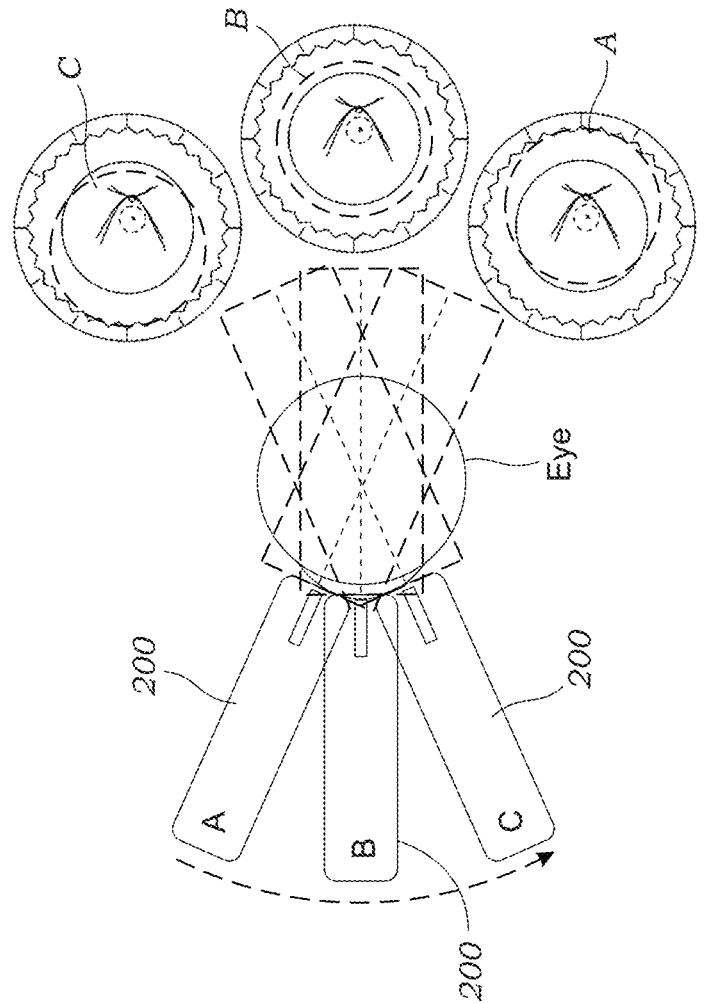

FIG. 17 illustrates the various scan directions that may be performed by universal actuator 10. Also illustrated are the en face scanned are of the eye for the radial scan, vertical raster scan, and horizontal raster scan. The horizontal raster scan of the eye is done using the motion imparted to the imaging probe 200 by the linear actuator 76. A vertical raster scan is performed by movement of the scissor platform 72. A radial scan of the eye is performed by the rotational actuator 84. The corresponding eye scans by the ultrasound probe 200 is schematically illustrated in FIG. 17. FIG. 19 illustrates how combining different images obtained at different rotational (pivot) angles of the imaging probe 200 relative to the eye is able to create a large field-of-view. The dashed lines A, B, C illustrate the FOVs generated by the particular orientation (A, B, C) of the imaging probe 200. A larger view of the eye with a plurality of FOVs superimposed on one another (composite en face scanned area) illustrates how combining images obtained at different pivoting orientations generates a much larger FOV as compared to a single scan.

Universal Actuator—Pivoting & Axial Rotation Scan #2

Figure 20B:
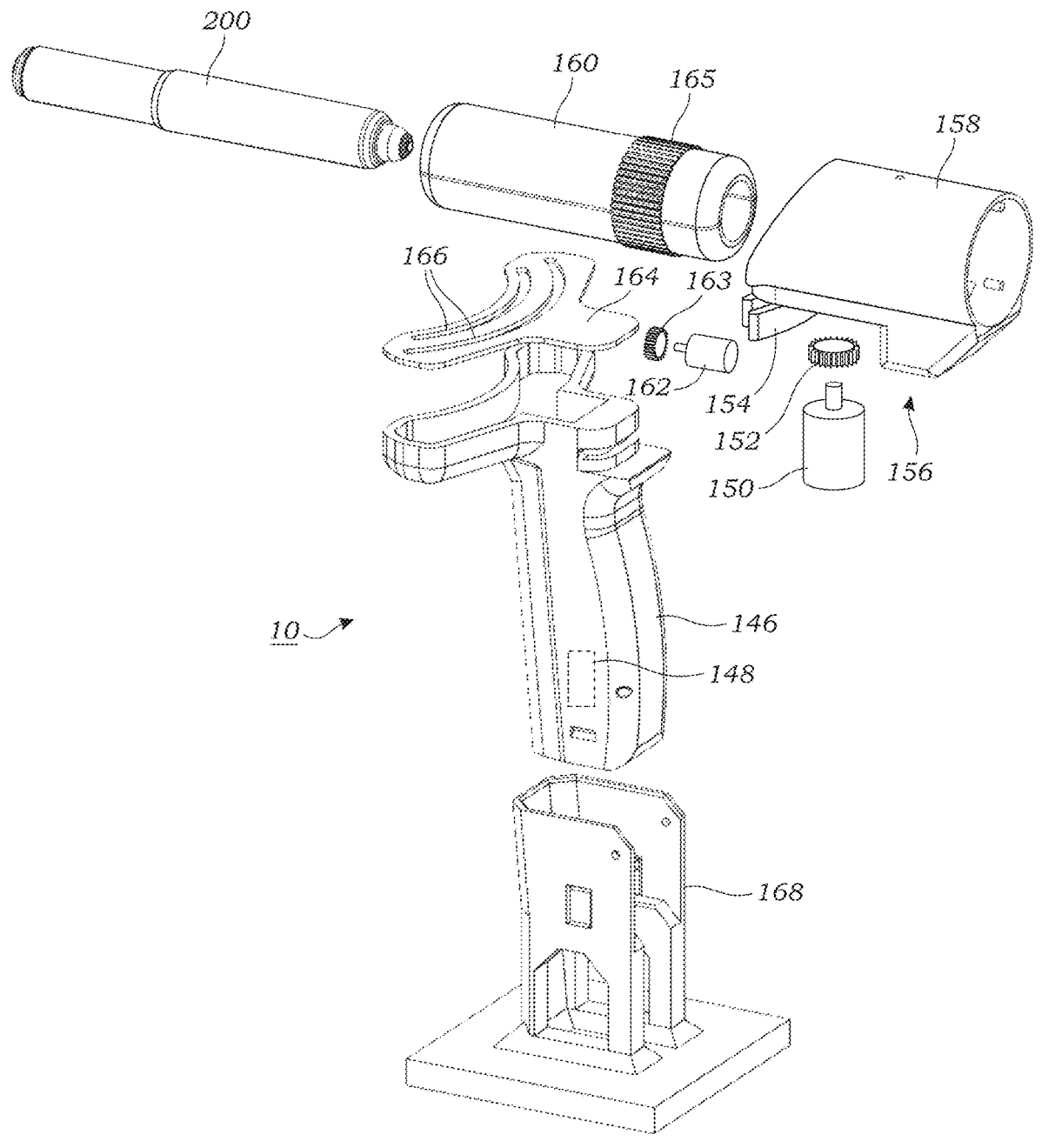
FIG. 20B illustrates an exploded view of the universal actuator of FIG. 20A.
Figure 20C:
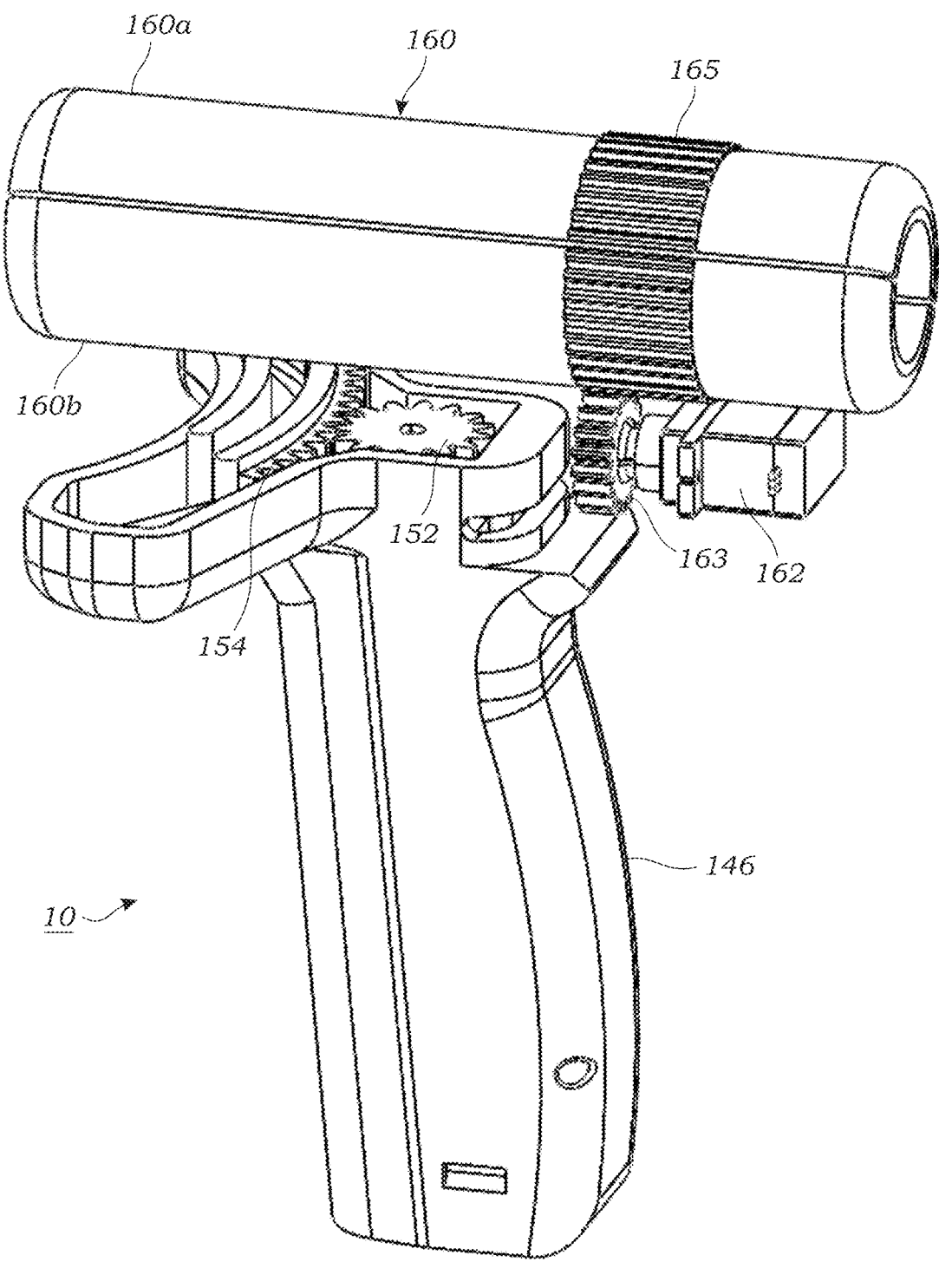
FIG. 20C illustrates a perspective view of the universal actuator of FIGS. 20A and 20B illustrating the pinion gear interfacing with the curved rack. Also illustrated are the servo motor and gear used to rotate the rotatable probe adapter via the geared surface on the exterior thereof.
Figure 20D:
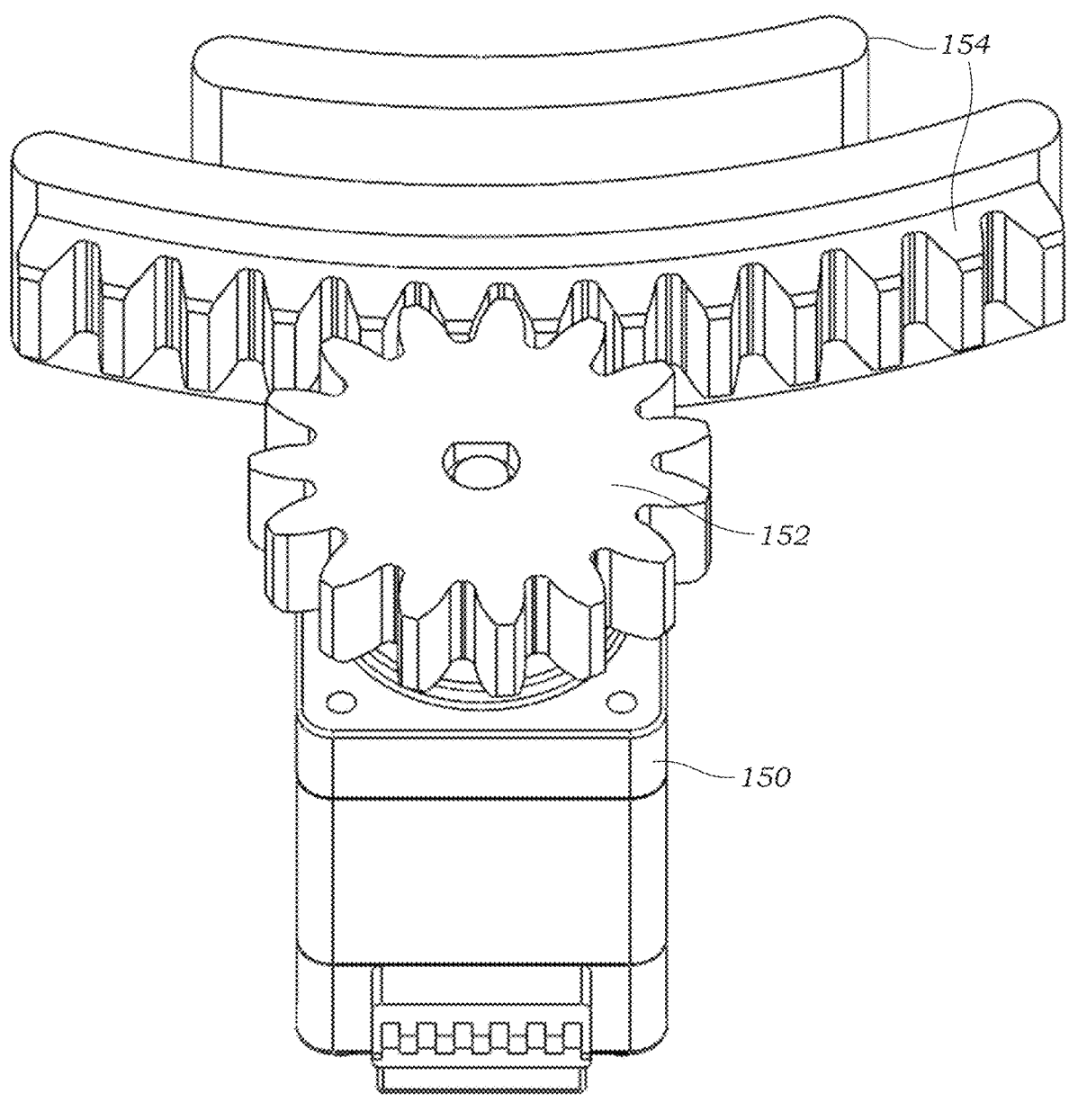
FIG. 20D illustrates how the mechanical interface of the pinion gear and the curved rack of the embodiment of FIGS. 20A-20C.

FIGS. 20A-20D illustrate an embodiment of a hand-held universal actuator 10. In this embodiment, with reference to FIG. 20B, the universal actuator 10 includes a handle 146 that that holds a power source 148 (e.g., battery) and a stepper motor 150. The stepper motor 150 rotates a pinion gear 152 that interfaces with a curved rack 154 that is connected to a rotational actuator 156 (FIGS. 20B-20D). The rotational actuator 156 includes a sleeve 158 that accommodates a rotatable probe adapter 160 that is rotated within the sleeve 158. The rotatable probe adapter 160 accommodates the imagine probe 200. The rotatable probe adapter 160 may include the two-part construction (e.g., halves 160a, 160b) similar to the probe adapter 94 and associated halves 100a, 100b described previously. A servo motor 162 is used to rotate the rotatable probe adapter 160 with gear 163 that interfaces with a geared surface 165 that is located about the periphery of the probe adapter 160 (best seen in FIG. 20C). The servo motor 162 and the gear 163 may be located within the body or housing of the sleeve 158. The handle 146 includes a flat upper surface 164 including grooves 166 which act as guides for the curved rack 154 and connected rotational actuator 156. One or more buttons (not shown) on the handle 146 may initiate the pivoting motion of the imaging probe 200 as well as the rotational motion of the imaging probe 200. Because the universal actuator 10 is hand-held, the user may also perform horizontal and/or vertical scans of the eye by moving the handle 146 accordingly. The hand-held universal actuator 10 is mountable within a base mount 168. The base mount 168 may be secured to the scissor platform 72 or the linear actuator 76. For example, the base mount 168 may be secured to the platform 82 of the embodiments illustrated in FIGS. 10 and 12. In this regard, the hand-held universal actuator 10 may be used in the multi-axis scan embodiment illustrated, for example, in FIG. 10. The scissor platform 72 provides the vertical movement while the linear actuator 76 provides the horizontal movement. The universal actuator 10 produces the pivoting movement as well as the axial rotation. The universal actuator 10 of FIGS. 20A-20D may be removable from the base mount 168 so that the universal actuator 10 can be used in the automatic scan mode or may be manually held to perform scans on the eye.

Figure 21:
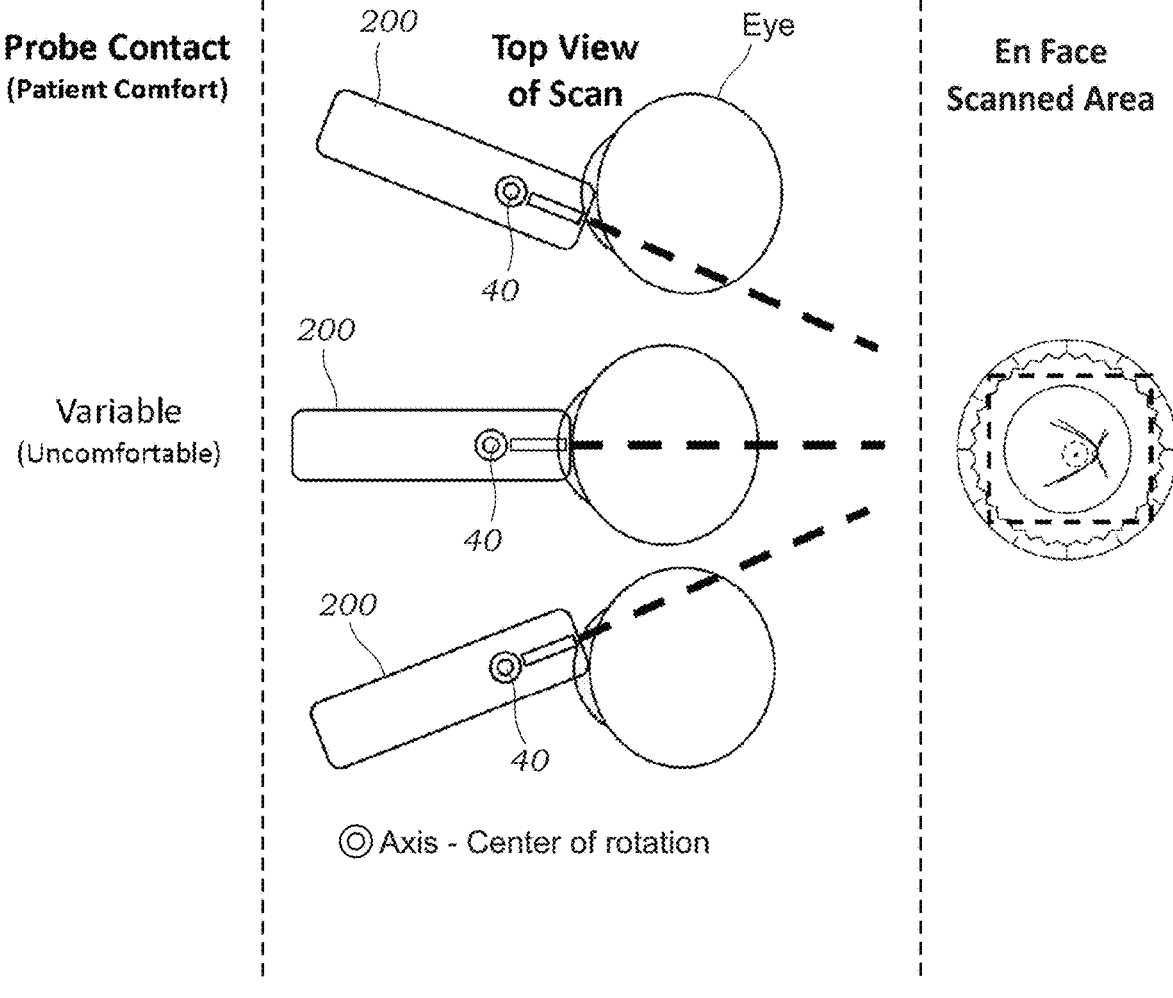
FIG. 21 illustrates various positions of an imaging probe relative to the eye in which the pivot axis is located through the imaging probe. The en face scanned area of the eye is also illustrated with the dashed line showing the field-of-view.
Figure 22:
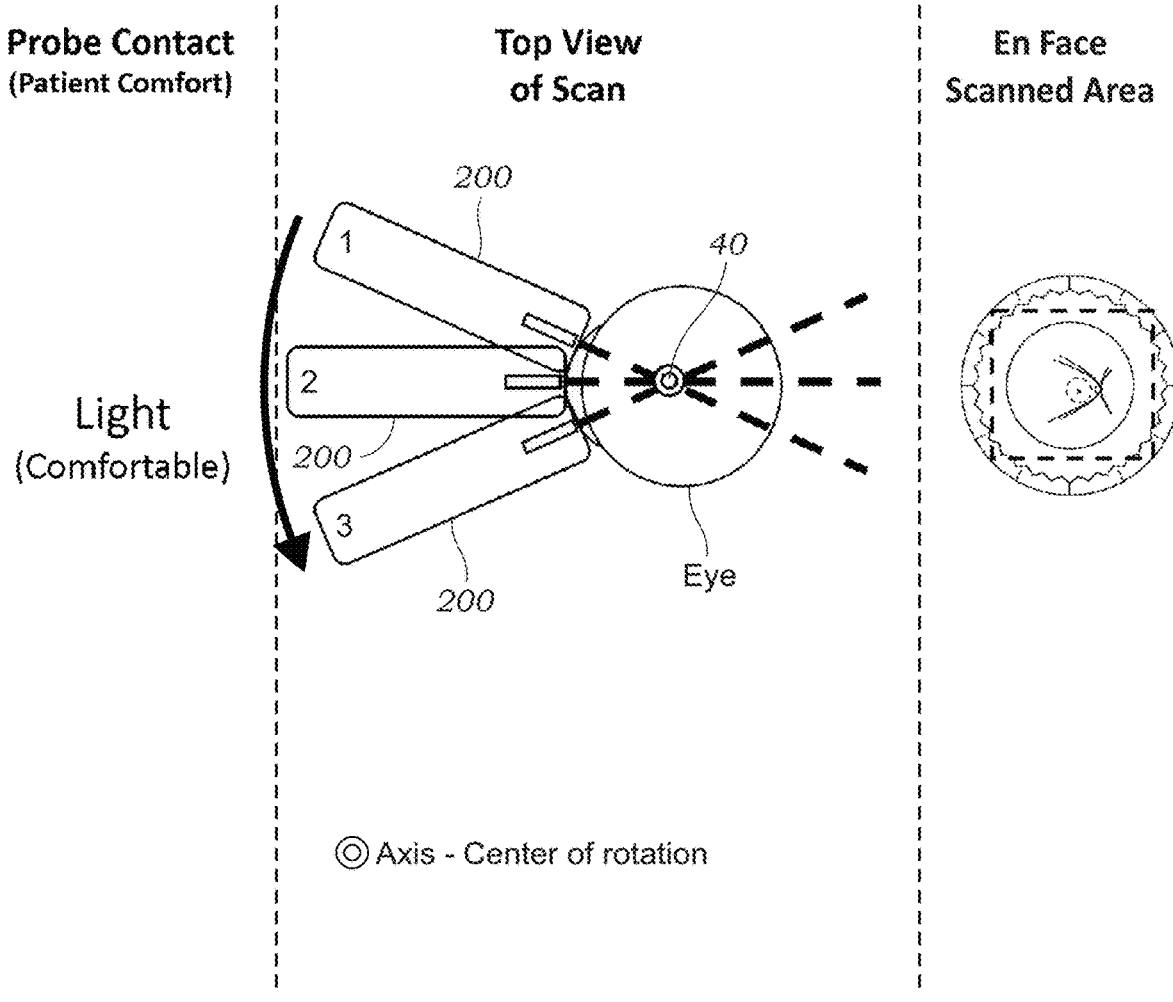
FIG. 22 illustrates various positions of an imaging probe relative to the eye in which the pivot axis is located within the eye of a subject. The en face scanned area of the eye is also illustrated with the dashed line showing the field-of-view.

In this embodiment, the pivot axis 40 of the imaging probe 200 is located within the eye itself. This is unlike the universal actuator 10 of FIGS. 10-17 in which the pivot axis is located through the imaging probe 200 itself. FIG. 21 illustrates various positions of the imaging probe 200 relative to the eye in which the pivot axis 40 is located through the imaging probe 200. The en face scanned area of the eye is also illustrated with the dashed line showing the field-of-view). FIG. 21 illustrates how patient comfort may be adversely impacted in certain positions of the imaging probe 200 which may be uncomfortable to the patient when the pivot axis 40 lies inside the imaging probe 200. During the pivoting movement, the imaging probe 200 may make hard contact with the surface of the eye which can be uncomfortable to some patients. FIG. 22 illustrates how patient comfort may be improved by a configuration in which the pivot axis 40 is located within the eye itself. Here the pivoting movement of the imaging probe 200 results in a light contact with the eye surface making the scan more comfortable. The hand-held universal actuator 10 of the embodiment of FIGS. 19 and 20 has a pivot axis 40 that passes through the eye.

While embodiments of the present invention have been shown and described, various modifications may be made without departing from the scope of the present invention. The invention, therefore, should not be limited, except to the following claims, and their equivalents.

What is claimed is:

1. A universal actuator for moving an imaging probe in a controlled manner to acquire a plurality of images of an eye comprising:
   a vertical direction actuator;
   a horizontal direction actuator;
   a rotational actuator mounted on one of the horizontal direction actuator or the vertical direction actuator, the rotational actuator comprising a first motor configured to rotate a universal rotation sleeve within the rotational actuator, wherein the universal rotation sleeve is secured to a probe adapter configured to hold the imaging probe therein; and
   a pivoting actuator configured to pivot the imaging probe along an arc, pivoting actuator comprises a second motor mechanically coupled to a pinion gear and wherein the rotational actuator is coupled to a curved rack that engages with the pinion gear, the curved rack being mechanically coupled to the rotational actuator.

2. The universal actuator of claim 1, wherein the first motor is coupled to a drive gear that engages with teeth on the universal rotation sleeve.

3. The universal actuator of claim 1, wherein the probe adapter and the universal rotation sleeve are secured to one another via respective keyed surfaces located on the universal rotation sleeve and the probe adapter.

4. The universal actuator of claim 1, wherein the probe adapter comprises a first half and a second half, the first and second halves comprising a recess therein dimensioned to accommodate the imaging probe.

5. The universal actuator of claim 4, further comprising a locking ring surrounding the first half and the second half of the probe adapter.

6. The universal actuator of claim 1, further comprising the imaging probe disposed inside the probe adapter.

7. The universal actuator of claim 1, wherein the imaging probe pivots about an axis of rotation that is located through the imaging probe.

8. The universal actuator of claim 1, wherein the imaging probe pivots about an axis of rotation that is located through the eye.

9. A method of using the universal actuator of claim 1 comprising:
   positioning the imaging probe adjacent to an eye of the subject; and
   obtaining a plurality of images of the eye with the imaging probe while moving the imaging probe in one or more of a horizontal direction, a vertical direction, a rotational direction, and/or a pivoting direction.

10. The method of claim 9, further comprising generating a three-dimensional (3D) image reconstruction or model of the eye from the plurality of images.

11. A universal actuator for moving an imaging probe in a controlled manner to acquire a plurality of images of an eye comprising:
   a housing containing a motor mechanically coupled to a pinion gear;

an imaging probe receiver coupled to a curved rack engaging with the pinion gear;

a pivot collar mounted at a distal end of the housing, the pivot collar pivotably secured to the housing via respective pins and forming a pivot axis;

the imaging probe having a proximal end engaged with the imaging probe receiver and a distal end engaged with the pivot collar; and a controller configured to drive the motor to move the curved rack back-and-forth along an arc and cause the distal end of the imaging probe to pivot about the pivot axis.

12. The universal actuator of claim 11, further comprising guide rails or slots disposed on the housing and interfacing with a pin disposed on the imaging probe receiver.

13. The universal actuator of claim 11, wherein the imaging probe pivots along a sweep angle between 10° and 40°.

14. A method of using the universal actuator of claim 11 comprising:

inserting the imaging probe into the imaging probe receiver and the pivot collar;

rotating the pinion gear to rotate the probe about the pivot axis; and acquiring a plurality of images or a movie of the eye with the imaging probe at a plurality of different pivot angles.

15. The method of claim 14, further comprising generating a three-dimensional (3D) image reconstruction or model of the object from the plurality of images or the movie.

16. The universal actuator of claim 11, wherein the universal actuator is a hand-held device.

17. A universal actuator for moving an imaging device in a controlled manner to acquire a plurality of images of an eye or face comprising:

a housing having a first surface for holding a rotatable platform comprising an imaging device mount disposed thereon and configured to hold the imaging device, the rotatable platform mechanically coupled to a rotary motor;

a slit lamp microscope comprising a face support defined by opposing vertical supports and a chin support; and an interface extending from a second side of the housing opposite the first side and comprising a plurality of rotatable fins or tabs located at the peripheral regions thereof, wherein the interface is positioned between the opposing vertical supports and wherein the rotatable fins or tabs are extended and secure the universal actuator to the face support.

18. The universal actuator of claim 17, further comprising an imaging device mounted on the imaging device mount.

19. A method of using the universal actuator of claim 17, comprising:

securing the imaging device to the image device mount;

moving the imaging device in a rotational direction; and acquiring a plurality of images or a movie of an eye or face with the imaging device during rotation of the rotatable platform.

20. The method of claim 19, further comprising generating a three-dimensional (3D) image reconstruction or model of the object from the plurality of images or the movie.

* * * * *